(12) United States Patent
Ishii et al.

(10) Patent No.: US 10,115,557 B2
(45) Date of Patent: Oct. 30, 2018

(54) X-RAY GENERATION DEVICE HAVING MULTIPLE METAL TARGET MEMBERS

(71) Applicant: HAMAMATSU PHOTONICS K.K., Hamamatsu-shi, Shizuoka (JP)

(72) Inventors: Atsushi Ishii, Hamamatsu (JP); Naonobu Suzuki, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 114 days.

(21) Appl. No.: 15/029,078

(22) PCT Filed: Sep. 3, 2014

(86) PCT No.: PCT/JP2014/073224
§ 371 (c)(1),
(2) Date: Apr. 13, 2016

(87) PCT Pub. No.: WO2015/056493
PCT Pub. Date: Apr. 23, 2015

(65) Prior Publication Data
US 2016/0233046 A1 Aug. 11, 2016

(30) Foreign Application Priority Data
Oct. 16, 2013 (JP) .................................. 2013-215499

(51) Int. Cl.
*H01J 35/08* (2006.01)
*H01J 35/32* (2006.01)
(Continued)

(52) U.S. Cl.
CPC ................ *H01J 35/08* (2013.01); *H01J 1/88* (2013.01); *H01J 1/92* (2013.01); *H01J 1/94* (2013.01);
(Continued)

(58) Field of Classification Search
CPC ........... A61B 6/00; A61B 6/40; A61B 6/4021; A61B 6/44; A61B 6/54; A61B 6/547;
(Continued)

(56) References Cited

U.S. PATENT DOCUMENTS

| 4,007,375 A | 2/1977 | Albert |
| 2012/0269323 A1 | 10/2012 | Adler et al. |
| 2015/0117616 A1* | 4/2015 | Ishii ........................ H01J 35/08 378/137 |

FOREIGN PATENT DOCUMENTS

| GB | 2473137 | 3/2011 |
| JP | H06-188092 A | 7/1994 |

(Continued)

OTHER PUBLICATIONS

English-language translation of International Preliminary Report on Patentability (IPRP) dated Apr. 28, 2016 that issued in WO Patent Application No. PCT/JP2014/073224.

*Primary Examiner* — Anastasia Midkiff
(74) *Attorney, Agent, or Firm* — Drinker Biddle & Reath LLP

(57) ABSTRACT

An X-ray generation device which can be efficiently used is provided. The X-ray generation device has an electron gun, a target unit, a tubular portion, a reflected electron detector, and a coil unit. The target unit includes a plurality of targets and a plurality of mark portions having a predetermined relationship with the targets, wherein each mark portion having a surface area larger than a surface area of the target when said target unit is viewed from a direction which is normal to principal faces of the target unit.

9 Claims, 21 Drawing Sheets

(51) Int. Cl.
| | |
|---|---|
| *H05G 1/52* | (2006.01) |
| *H01J 1/88* | (2006.01) |
| *H01J 19/32* | (2006.01) |
| *H01J 37/14* | (2006.01) |
| *H01J 1/92* | (2006.01) |
| *H01J 1/94* | (2006.01) |
| *H01J 19/46* | (2006.01) |
| *H01J 19/48* | (2006.01) |
| *H01J 37/147* | (2006.01) |
| *A61B 6/00* | (2006.01) |
| *H01J 3/26* | (2006.01) |
| *H01J 21/36* | (2006.01) |
| *H01J 35/14* | (2006.01) |

(52) U.S. Cl.
CPC .............. *H01J 19/32* (2013.01); *H01J 19/46* (2013.01); *H01J 19/48* (2013.01); *H01J 35/32* (2013.01); *H01J 37/1472* (2013.01); *H05G 1/52* (2013.01); *A61B 6/547* (2013.01); *H01J 3/26* (2013.01); *H01J 21/36* (2013.01); *H01J 35/14* (2013.01); *H01J 2235/08* (2013.01); *H01J 2235/081* (2013.01); *H01J 2235/086* (2013.01); *H01J 2235/087* (2013.01); *H01J 2235/088* (2013.01); *H01J 2235/186* (2013.01); *H01J 2237/032* (2013.01); *H01J 2237/036* (2013.01); *H01J 2893/0003* (2013.01); *H01J 2893/0051* (2013.01); *H01J 2893/0052* (2013.01)

(58) Field of Classification Search
CPC .. H05G 1/00; H05G 1/02; H05G 1/26; H05G 1/30; H05G 1/52; H01J 1/00; H01J 1/02; H01J 1/36; H01J 1/46; H01J 1/88; H01J 1/92; H01J 1/94; H01J 3/00; H01J 3/02; H01J 3/027; H01J 3/029; H01J 3/26; H01J 3/28; H01J 3/30; H01J 3/38; H01J 19/00; H01J 19/02; H01J 19/28; H01J 19/32; H01J 19/38; H01J 19/42; H01J 19/46; H01J 19/48; H01J 21/00; H01J 21/02; H01J 21/06; H01J 21/36; H01J 2237/00; H01J 2237/03; H01J 2237/032; H01J 2237/036; H01J 2237/04; H01J 2237/06; H01J 2237/061; H01J 2237/151; H01J 2237/1518; H01J 2893/00; H01J 2893/0001–2893/0003; H01J 2893/0005; H01J 2893/0006; H01J 2893/0012; H01J 2893/003; H01J 2893/0048; H01J 2893/0051; H01J 2893/0052; H01J 35/00; H01J 35/02; H01J 35/04; H01J 35/08; H01J 35/16; H01J 35/18; H01J 35/24; H01J 35/30; H01J 35/32; H01J 37/00; H01J 37/02; H01J 37/147; H01J 37/1472; H01J 37/1474; H01J 37/1477; H01J 2235/00; H01J 2235/02; H01J 2235/08; H01J 2235/083; H01J 2235/086–2235/088; H01J 2235/186

See application file for complete search history.

(56) References Cited

FOREIGN PATENT DOCUMENTS

| | | |
|---|---|---|
| JP | 2004-028845 A | 1/2004 |
| JP | 2011-077027 A | 4/2011 |
| JP | 2012-054045 A | 3/2012 |
| TW | 200400780 | 1/2004 |
| TW | 200802488 | 1/2008 |

* cited by examiner

X-RAY GENERATION DEVICE HAVING MULTIPLE METAL TARGET MEMBERS

TECHNICAL FIELD

The present invention relates to an X-ray generation device.

BACKGROUND ART

As a known target unit for generation of X-rays provided in an X-ray generation device, there is a target unit including a substrate and a target buried in the substrate (e.g., cf. Patent Literature 1: Japanese Unexamined Patent Publication No. 2004-028845). In the target unit for generation of X-rays described in Patent Literature 1, a single columnar metal wire comprised of tungsten or molybdenum is buried in the substrate comprised of a light element such as beryllium or carbon.

SUMMARY OF INVENTION

Technical Problem

For meeting the need for further reduction in X-ray focal spot size, it is necessary to further reduce the size of the target. On the other hand, when the target is formed in a smaller size (e.g., nanometer size), it becomes necessary to specify the location of the target in the target unit, in order to make a focused electron beam incident to the target. For that purpose, it is conceivable, for example, to implement scanning on the target unit with the electron beam and specify the location of the target with use of information obtained thereby. However, since the target is microscopic, a signal amount (signal variation amount) obtained by the scanning is also small; therefore, for obtaining the necessary information, it is necessary to accurately certainly detect a faint signal (signal variation). For that, it is necessary to lower the speed of the scanning. As just described, it is not easy to specify the location of the target and some time is required to specify the location. Furthermore, as the size of the target decreases, influence of heat of the electron beam or the like becomes more prominent, so as to shorten the lifetime of the target. For this reason, it is necessary to frequently replace the target unit and it is difficult to efficiently use the X-ray generation device.

It is an object of the present invention to provide an X-ray generation device that can be efficiently used.

Solution to Problem

An X-ray generation device according to one aspect of the present invention comprises: an electron gun for emitting an electron beam; a target unit having a target buried in a substrate having principal faces opposed to each other; a housing at one end side of which the target unit is arranged and at the other end side opposed to the one end side of which the electron gun is arranged, the housing having an electron passage for the electron beam to pass; a deflector for deflecting the electron beam passing in the electron passage, so as to enable scanning on the target unit; and a signal acquisition unit for acquiring an incident signal generated based on the electron beam in the scanning on the target unit, wherein the target unit comprises: a plurality of first metal members serving as the target; and a second metal member having a predetermined location relationship with the first metal members and, when viewed from a normal direction to the principal faces, having a surface area larger than a surface area of the first metal member, and wherein the deflector makes the electron beam passing in the electron passage, incident to the first metal member, based on the incident signal acquired by the signal acquisition unit.

In this X-ray generation device, the target unit includes the second metal member having the predetermined location relationship with the first metal members serving as the target (the first metal member will also be referred to hereinafter simply as target) and the second metal member has the surface area larger than that of the first metal member, when viewed from the normal direction to the principal faces. This enables the device to certainly generate the location information (incident signal) of the second metal member having the predetermined location relationship with the first metal members, on occasions of the scanning on the target unit with the electron beam. Therefore, the X-ray generation device is able to specify the location of the first metal member, based on the location of the second metal member easier to detect, and thus the electron beam can be made quickly and accurately incident to the target by the deflector. Since a plurality of targets are arranged in the target unit, even if one target becomes deteriorated due to heat or the like, another target can be used by deflecting the electron beam thereto by the deflector, and thus there is no need for replacing the target unit every time one target becomes deteriorated. Therefore, a frequency of replacement of the target unit can be lowered and thus the X-ray generation device can be efficiently used.

In one embodiment, a plurality of second metal members may be arranged with regularity. Since this configuration enables the device to readily perform movement to the next second metal member (detection of the second metal member), it can efficiently generate X-rays.

In one embodiment, the plurality of first metal members may be arranged with regularity. Since this configuration enables the device to readily perform movement to the next target (specification of the target), it can efficiently generate X-rays.

In one embodiment, the predetermined location relationship may be that either one of the first metal members and the second metal member is arranged surrounding the other. Since this configuration clarifies a region where the target is arranged, the device can readily perform the specification of the target. Therefore, X-rays can be efficiently generated.

In one embodiment, the predetermined location relationship may be that the first metal members are arranged along an arrangement direction of the second metal member. Since this configuration clarifies the region where the target is arranged, the device can readily perform the specification of the target. Therefore, X-rays can be efficiently generated.

In one embodiment, the X-ray generation device may comprise at least two second metal members, and one of the second metal members may have location information indicative of a location of the other of the second metal members. Since this configuration enables the device to readily perform movement to the next second metal member (detection of the second metal member), it can efficiently generate X-rays.

In one embodiment, the second metal member may have a configuration indicative of a direction in which the first metal member is arranged. Since this configuration clarifies the region where the target is arranged, the device can readily perform the specification of the target. Therefore, X-rays can be efficiently generated.

Advantageous Effects of Invention

The present invention has enabled efficient use of the X-ray generation device.

DESCRIPTION OF EMBODIMENTS

Embodiments of the present invention will be described below in detail with reference to the accompanying drawings. It is noted that throughout the description of the drawings identical or equivalent elements will be denoted by the same reference signs, without redundant description.

First Embodiment

Figure 1:
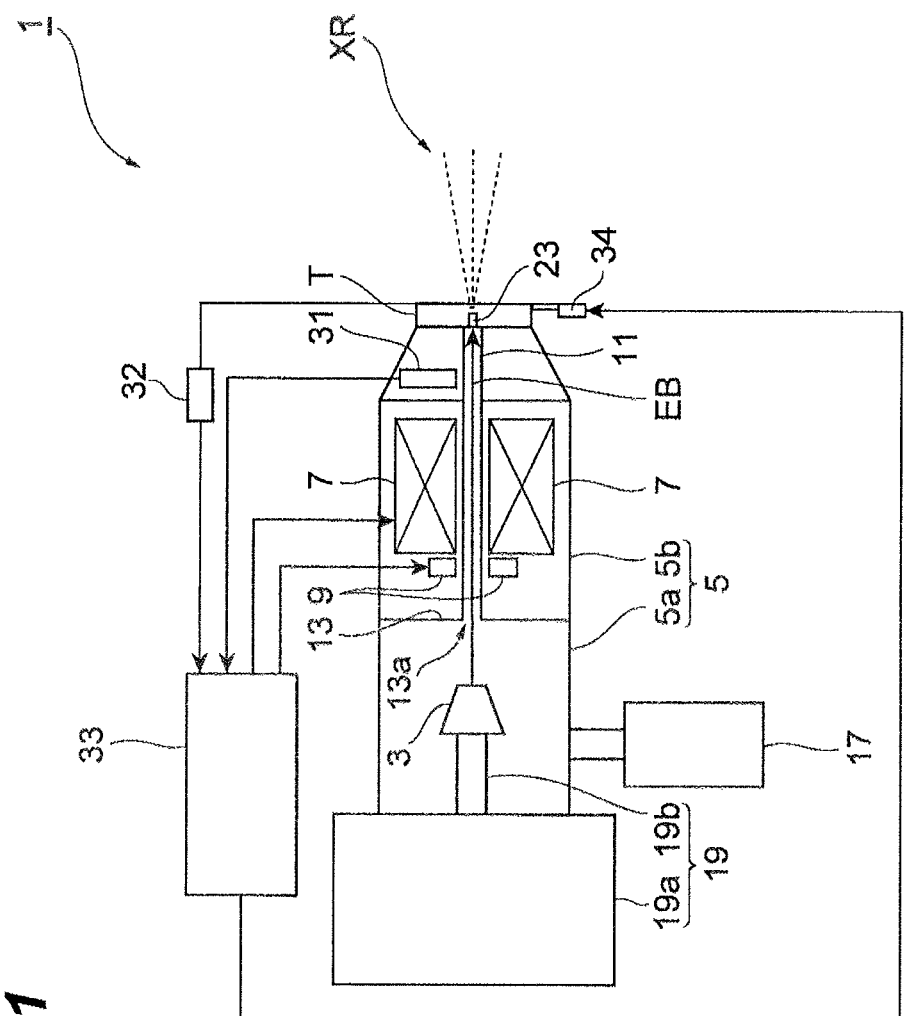
FIG. 1 is a schematic configuration diagram showing the X-ray generation device according to the first embodiment.

The configuration of the X-ray generation device according to the present embodiment will be described with reference to FIG. 1. FIG. 1 is a schematic configuration diagram showing the X-ray generation device according to the first embodiment.

The X-ray generation device 1 is an, open type capable of creating a vacuum state as needed, different from a disposable sealed type, thereby to permit replacement of a target unit T, a cathode of an electron gun 3, and so on. The X-ray generation device 1 has a tubular portion (housing) 5 of a cylindrical shape which is brought into a vacuum state during operation and which is comprised of an electroconductive material, e.g., stainless steel. The tubular portion 5 consists of an electron gun receiver 5*a* located on the lower side and a target holder 5*b* located on the upper side, and the target holder 5*b* is attached to the electron gun receiver 5*a* through a hinge (not shown). Therefore, when the target holder 5*b* is rotated into a horizontal tilt state through the hinge, the top of the electron gun receiver 5*a* can be made open, so as to allow access to the electron gun 3 (cathode) received in the electron gun receiver 5*a*.

Provided inside the target holder 5*b* are a tubular coil unit 7 functioning as a focusing lens and a tubular coil unit (deflector) 9 functioning as a deflection coil. Inside the target holder 5*b* an electron passage 11 extends in the longitudinal direction of the tubular portion 5 so as to pass through the center of the coil units 7, 9. The electron passage 11 is surrounded by the coil units 7, 9. A disk plate 13 is fixed to the lower end of the target holder 5*b* so as to lid it. An electron inlet hole 13*a* in line with the lower end of the electron passage 11 is formed at the center of the disk plate 13.

The upper, end of the target holder 5*b* is formed in a circular truncated cone and the target unit T of a transmission type is mounted on the top of the target holder 5*b* while being located at the upper end side of the electron passage 11 and forming an X-ray exit window. Since the target unit T is detachably fixed in a grounded state through an unillustrated detachment structure so as to vacuum-seal the upper end of the electron passage 11, it is also feasible to replace the target unit T with another as an expendable part.

A vacuum pump 17 is fixed to the electron gun receiver 5*a* and the vacuum pump 17 functions to evacuate the interior of the tubular portion 5 to achieve a high vacuum state. Namely, since the X-ray generation device 1 is equipped with the vacuum pump 17, we are allowed to replace the target unit T, the cathode, and so on.

A molded power supply unit 19 integrated with the electron gun 3 is fixed to the base end side of the tubular portion 5. The molded power supply unit 19 is a unit that is formed by molding with an electrically insulating resin (e.g., epoxy resin) and that is received in a metal case.

A high-voltage generator (not shown) constituting such a transformer as to generate a high voltage (e.g.,—several ten kV or less) is enclosed in the molded power supply unit 19. The molded power supply unit 19 has a power supply main body 19*a* of a block form located on the lower side and having a rectangular parallelepiped shape, and a neck portion 19*b* of a circular column shape projecting upward from the power supply main body 19*a* into the electron gun receiver 5*a*. The high-voltage generator is enclosed in the power supply main body 19a with the electrically insulating resin. The electron gun 3 arranged opposite to the target unit T is mounted at the tip of the neck portion 19b so as to interpose the electron passage 11 between them. An electron emission controller (not shown) electrically connected to the high-voltage generator is enclosed in the power supply main body 19a of the molded power supply unit 19. The electron emission controller is connected to the electron gun 3 and controls the timing of emission of electrons, tube current, and so on.

Figure 2:
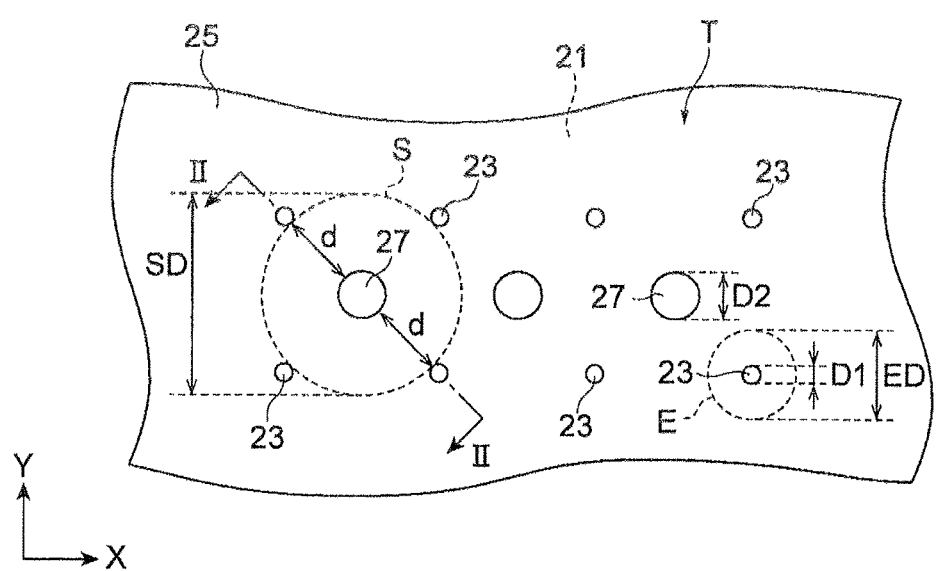
FIG. 2 is a view of a target unit viewed from a first principal face side of a substrate.
Figure 3:
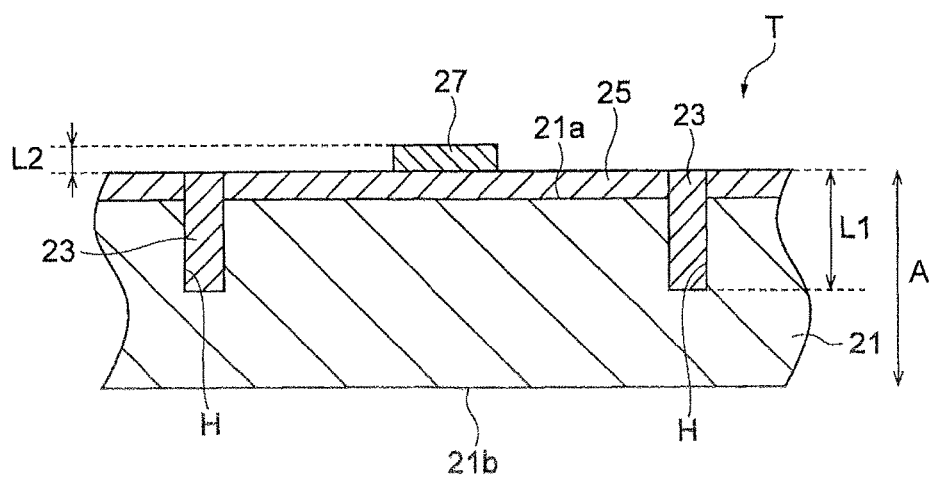
FIG. 3 is a drawing showing a cross-sectional configuration along the line II-II in FIG. 2.

Next, the target unit T will be described. FIG. 2 is a view of the target unit viewed from the first principal face side of the substrate. FIG. 3 is a drawing showing a cross-sectional configuration along the line II-II in FIG. 2. It should be noted that, concerning the target units T to T10 hereinafter, the size of each component, separation distance, etc. on the illustration do not always conform with actual numerical conditions, for facilitating the illustration. Namely, in each drawing, a dimensional ratio of each component may be different from an actual one and thus it does not always agree with an actual component. The description hereinbelow will be given using the directions shown in the drawing (X-direction and Y-direction).

As shown in FIG. 2 and FIG. 3, the target unit T has a substrate 21, targets (first metal members) 23, an electroconductive layer 25, and mark portions (second metal members) 27, and is configured as a transmission type target also serving as an X-ray exit window. The substrate 21 is comprised of an electrically insulating material with little generation of X-rays upon incidence of electrons and with excellent radio-transparency and heat radiation performance, e.g., diamond. The substrate 21 has first and second principal faces 21a, 21b of planes, as principal faces opposed to each other, and is thus a flat plate member. The first principal face 21a is a face on the electron incidence side and the second principal face 21b is a face on the X-ray exit side. The thickness of the substrate 21 in a direction along a normal direction A to the first and second principal faces 21a, 21b is set, for example, to about 300 µm.

The targets 23 are located on the first principal face 21a side of the substrate 21. The targets 23 are buried in holes extending in the normal direction A in the substrate 21 and, specifically, buried in respective holes H formed in a shape with bottom from the first principal face 21a side. The targets 23 are comprised of a material different from the substrate 21. The targets 23 are formed in a circular column shape of a metal that generates X-rays upon incidence of an electron beam EB (e.g., tungsten, gold, platinum, or the like). The targets 23 have, for example, the following dimensions: an outer size (diameter) D1 of an electron incidence face being an end face on the first principal face 21a side viewed from the normal direction A is approximately from 100 nm to 2 µm and a length (thickness) L1 in the direction along the normal direction A is approximately from 500 nm to 4 µm. In the present embodiment, tungsten is adopted as the metal of the targets 23, the outer size D1 of the targets 23 is, for example, 500 nm, and the length L1, for example, 1 µm.

A plurality of targets 23 (eight targets herein) are arranged in the substrate 21 and the arrangement thereof has regularity. The targets 23 are arranged on the circumferences of virtual circles S centered at the below-described mark portions 27 and surround the mark portions 27. The targets 23 are arranged at respective positions opposite to each other with the mark portion 27 in between. The neighboring targets 23 on the virtual circumferences are located at equal intervals. In regard to only the targets 23, the targets 23 are arranged at predetermined intervals (equal intervals) on a straight line along the X-direction and are arranged at predetermined intervals (equal intervals) on a straight line along the Y-direction.

The electroconductive layer 25 is formed on the first principal face 21a side of the substrate 21 and functions to restrain charging of the first principal face 21a due to the electron beam EB and protect the first principal face 21a from the electron beam EB. The electroconductive layer 25 is comprised, for example, of an electroconductive material containing a transition element (more preferably, a first transition element) and, for example, is an electroconductive thin film comprised of titanium, chromium, or an electroconductive compound of them. In the present embodiment the electroconductive layer 25 is a titanium thin film. A length (thickness) of the electroconductive layer 25 in the direction along the normal direction A is, for example, about 50 nm and is smaller than the length L1 of the targets 23. The electroconductive layer 25 is formed, for example, by evaporation such as physical vapor deposition (PVD) on the first principal face 21a. The electroconductive layer 25 may be configured using diamond doped with an impurity (e.g., boron or the like) and, in this case, diamond particles are generated and grown by a microwave plasma CVD method to form a diamond layer and the diamond layer formed is doped with boron to form the electroconductive layer. In the present embodiment, the electroconductive layer 25 is formed so as to expose the electron incidence faces of the targets 23, but it may be formed so as to cover them.

The mark portions 27 are located on the first principal face 21a side of the substrate 21 and arranged on the electroconductive layer 25. The mark portions 27 are portions that generate location information as reference, on occasions of specifying the locations of the targets 23. The mark portions 27 are arranged as separated without overlapping the targets 23, when viewed from the normal direction A to the first and second principal faces 21a, 21b of the substrate 21. The mark portions 27 are of a substantially circular shape and a plurality of mark portions (three mark portions herein) are arranged. The mark portions 27 are arranged with a predetermined location relationship with the targets 23. Specifically, each of the mark portions 27 is arranged at the center of the virtual circle S with the circumference thereof passing the positions where the targets 23 are located, and is surrounded by the targets 23. In regard to only the mark portions 27, the mark portions 27 have regularity of arrangement thereof and are arranged at predetermined intervals (equal intervals) on a straight line along the X-direction. The mark portions 27 are formed on the electroconductive layer 25 in the present embodiment, but the mark portions 27 may be covered by the electroconductive layer 25.

Each of separation distances d between the mark portions 27 and the targets 23 (shortest distances between the opposed outer edges of the mark portions 27 and the targets 23) is, for example, approximately from 10 to 50 µm. When the outer size D1 of the targets 23 is sufficiently smaller than the separation distances d, the separation distances d may be approximated to the radius of the virtual circle S. The mark portions 27 are formed in a circular disk shape of a metal (e.g., tungsten, gold, platinum, or the like) consisting of a material different from the substrate 21. In the present embodiment, tungsten is adopted as the metal of the mark portions 27 as is adopted for the targets 23.

The mark portions 27 are formed in a flattened circular column shape, e.g., in such dimensions that an outer size (diameter) D2 on the view from the normal direction A is approximately from 3 to 10 µm and a length (thickness) L2 in the direction along the normal direction A is approximately from 50 to 500 nm. In the present embodiment, the outer size D2 of the mark portions 27 is, for example, 5 μm and the length L2, for example, 200 nm. The outer size D2 of the mark portions 27 is larger than the outer size D1 of the targets 23 (D2>D1). Namely, a surface area of the mark portion 27 (area on the view from the electron incidence side in the normal direction A to the first and second principal faces 21a, 21b of the substrate 21) is larger than a surface area of the target 23. The length L2 of the mark portion 27 is smaller than the length L1 of the target 23 (L2<L1) and is larger than the length of the electroconductive layer 25 in the direction along the normal direction A.

Reference is made again to FIG. 1. The X-ray generation device 1 includes a reflected electron detector 31 as a reflected electron detection unit (signal acquisition unit), a controller 33 as a control unit, and an XY stage 34 serving as a mechanical moving mechanism for the target unit T (targets 23). The reflected electron detector 31 is arranged at the upper end side of the target holder 5b so as to face the target unit T, at a position where it does not affect and is not affected by the electron beam EB directed toward the target unit T, through an unillustrated path or in the electron passage 11. The reflected electron detector 31 detects reflected electrons from the target unit T and acquires them as an incident signal generated based on the electron beam EB incident to the target unit T. The X-ray generation device may be provided with a current detector (incident signal acquisition unit) 32 as an absorbed electron detection unit. The current detector 32 is electrically connected to the target unit T, and functions to detect an absorbed current (incident signal) indicative of an amount of the electron beam. EB absorbed by the target unit T, and output information thereof to the controller 33 as a control unit. The X-ray generation device may be configured without the current detector as a separate unit, but the controller 33 may include the current detector. The X-ray generation device may be equipped with both of the reflected electron detection unit and the absorbed electron detection unit or with either one of them. Furthermore, the control unit may be the single controller 33 configured so as to perform the control on the X-ray generation device 1, or may include a plurality of controllers 33 configured so as to perform the control on the X-ray generation device 1 by cooperation of those controllers.

The controller 33 performs various controls on the X-ray generation device 1 and, for example, it controls the high-voltage generator and the electron emission controller in the molded power supply unit 19. This makes a predetermined electric current or voltage applied between the electron gun 3 and the target unit T (targets 23), whereby the electron beam EB is emitted from the electron gun 3. The electron beam EB emitted from the electron gun 3 is appropriately focused by the coil unit 7 under control of the controller 33 to impinge upon the target unit T to form a focused area on the target unit T. This focused area is an irradiation field E on the target unit T with the electron beam EB and is approximately equal to a region where an electron incidence trace is made upon incidence of the electron beam EB onto the target unit T. When the irradiation field B, as shown in FIG. 2, is viewed from the direction perpendicular to the target unit T (electron incidence direction), which extends along the normal direction A, the target 23 is included in the range thereof and the outer edge thereof is included in a separation area between the target 23 and the mark portion 27. Since the outer edge of the separation area is equal to the virtual circle S with the same center as the foregoing target 23, an outer size (diameter) ED of the irradiation field E is larger than the outer size D1 of the target 23 and smaller than the outer size (diameter) SD of the virtual circle S (D1<ED<SD). The outer size ED of the irradiation field E is, for example, approximately from 10 to 30 μm.

In this manner, when the irradiation field E being the focused area is located at the target 23, the mark portion 27 is arranged outside the area of the irradiation field E; for this reason, X-rays XR with a desired focal spot size can be extracted while suppressing a noise component due to the mark portion 27. In other words, when X-rays are extracted by irradiation on the target 23 with the electron beam EB, the controller 33 controls the coil unit 7 in such a manner that the irradiation field E can surely include the target 23 but not include the mark portion 27, whereby X-rays XR with a desired focal spot size can be extracted while suppressing the noise component due to the mark portion 27.

The controller 33 monitors the intensity of reflected electrons detected by the reflected electron detector 31 (or absorbed electrons detected by the current detector 32) in real time and controls the coil unit 9, based on the intensity of the reflected electrons (absorbed electrons) from the target unit T and the location information set in the target unit T. At this time, the coil unit 9 deflects the electron beam EB from the electron gun 3 in such a manner that the irradiation field E of the electron beam EB can two-dimensionally scan the surface on the target unit T. A scan area (range) on the target unit T by the electron beam EB in the scanning by the coil unit 9 is, for example, approximately from 100 to 150 μm. When the incidence region of the electron beam EB onto the target unit T is desired to be moved more than the scan area, the target unit T (targets 23) itself may be moved relative to the target holder 5b by the XY stage 34, based on control of the controller 33. In this manner, the targets 23 can be utilized in a wider range by combining the deflection of the electron beam EB by the coil unit 9 with the movement of the target unit T (targets 23) itself by the XY stage 34.

When a substance is irradiated with the electron beam EB, reflected electrons are emitted by an amount dependent on the atomic number of the substance (the greater the atomic number, the more the reflected electrons are emitted). Since in the present embodiment the targets 23 of tungsten and the mark portions 27 of tungsten are arranged on the substrate 21 of diamond, a place where a larger number of reflected electrons are detected can be determined to be a target 23 or a mark portion 27. Then, the controller 33 controls the deflection of the electron beam EB so as to obtain a larger number of reflected electrons.

On the other hand, when the substance is irradiated with the electron beam EB, it also absorbs electrons by an amount dependent on the atomic number of the substance. Namely, the greater the atomic number, the smaller the absorbed current value; or, the smaller the atomic number, the larger the absorbed current value. Since in the present embodiment the targets 23 of tungsten and the mark portions 27 of tungsten are provided on the substrate 21 of diamond, a place where the absorbed current value is smaller can be determined to be a target 23 or a mark portion 27. Then, the controller 33 controls the deflection of the electron beam EB so as to make the absorbed current value smaller. In the present embodiment, the absorbed current is equal to a target current.

Figure 4:
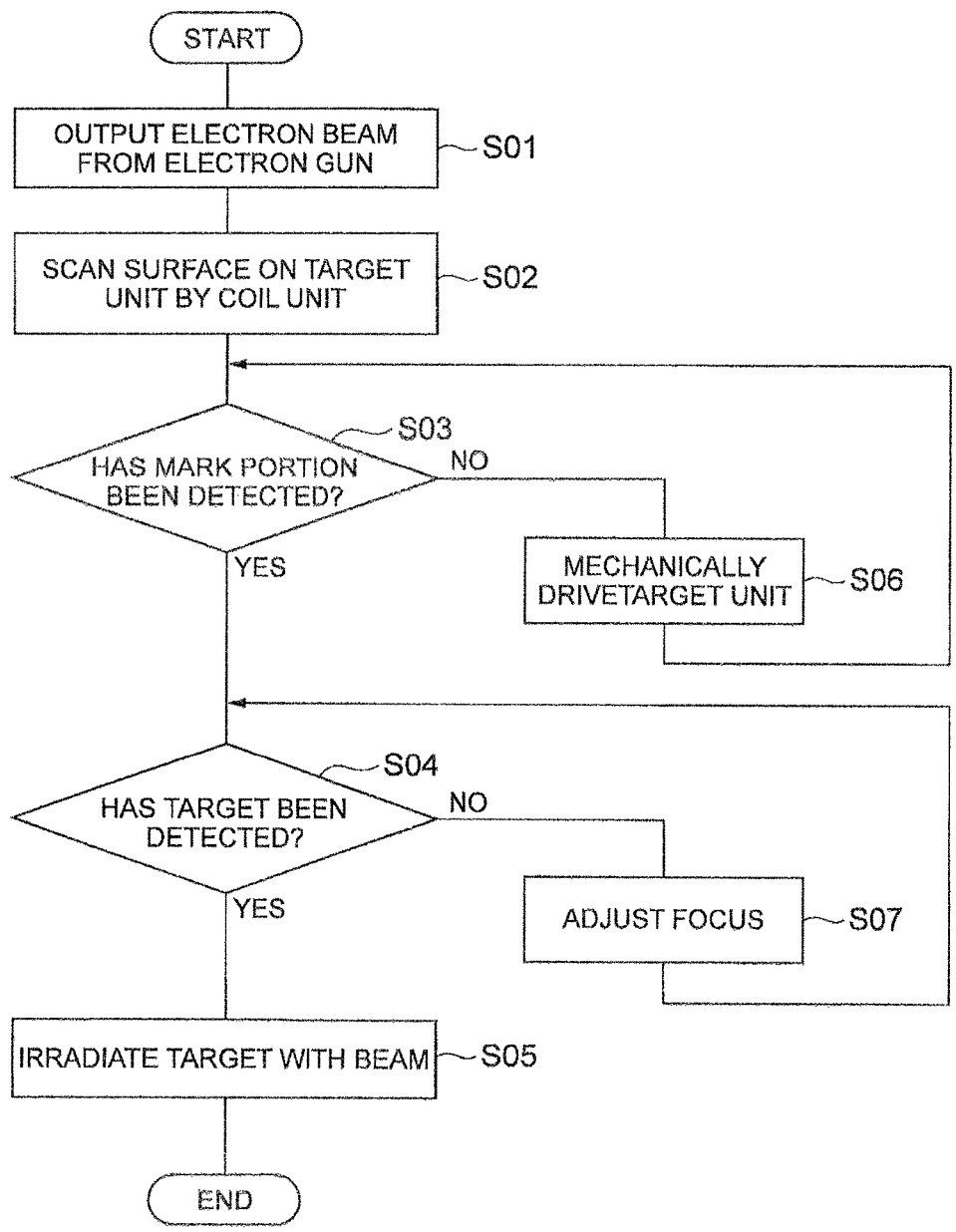
FIG. 4 is a flowchart showing a method to specify a target.

A method to specify a target 23 will be described in more detail. FIG. 4 is a flowchart showing the target specifying method.

As shown in FIG. 4, first, the electron gun 3 outputs the electron beam EB (step S01). Subsequently, the controller 33 controls the coil unit 9 as deflector to scan the surface on the target unit T with the electron beam EB (step S02). The surface is searched for a mark portion 27 while monitoring the intensity of reflected electrons detected by the reflected electron detector 31 (or absorbed electrons detected by the current detector 32), and whether a mark portion 27 has been detected is determined (step S03). Since in the target unit T the mark portion 27 has the larger surface area than the target 23, a variation in signal upon entrance of the mark portion 27 into the irradiation field E of the electron beam EB (variation in intensity of reflected electrons or absorbed electrons) is greater than a variation in signal upon entrance of the target 23 into the irradiation field E of the electron beam EB. For this reason, the location information of the mark portion 27 in the target unit T can be certainly acquired compared to the target 23. When it is determined that a mark portion 23 has been detected, the flow goes to step S04. On the other hand, when no mark portion 27 has been detected, the target unit T is moved by the XY stage 34 (step S06).

The controller 33, when acquiring the location information of the mark portion 27, assumes that the location where the mark portion 27 is arranged is the center of the circumference of a virtual circle where a plurality of targets 23 are located, and obtains the virtual circle centered at the mark portion 27. After obtaining the virtual circle, the controller 33 searches the surface for a location of a target 23, based on the location information on the circumference thereof and the location information of the targets 23 set in the target unit T and based on the intensity of signal (intensity of reflected electron or absorbed electrons), and whether a target 23 has been detected is determined (step S04). When it is determined that a target 23 has been detected, the controller 33 controls the coil unit 9 as deflector so as to locate the irradiation field of the electron beam EB at the target 23 (step S05). Alternatively, it may estimate the location of the target 23 from the location information of the mark portion 27 and perform precise re-scanning at a slower speed from a start point of the mark portion 27, thereby specifying the location of the target 23. On the other hand, when no target 23 has been detected, the coil unit 7 is controlled to adjust the focus of the electron beam ED (step S07). In the X-ray generation device 1, as described above, the location of the target 23 is specified in the target unit T and the target 23 is irradiated with the electron beam EB to generate X-rays with a desired focal spot size.

In the present embodiment, both of the target 23 and the mark portion 27 are made of tungsten, but the length (thickness) in the normal direction A of the mark portion 27 is smaller than the length (thickness) in the normal direction A of the target 23. For this reason, the intensity of reflected electrons (absorbed electrons) from the mark portion 27 is smaller than the intensity of reflected electrons (absorbed electrons) from the target 23. This allows the device to discriminate the target 23 and the mark portion 27 from each other even though they are made of the same material.

In the present embodiment, as described above, the surface area of the mark portion 27 is larger than that of the target 23. This allows the X-ray generation device 1 to certainly obtain the location information of the mark portion 27 which is the location information of the substance different from the substrate 21, in the target unit T. Since the targets 23 are arranged so as to surround the mark portion 27, the arrangement region of the targets 23 is clear. In the X-ray generation device 1, therefore, the location of the target 23 can be specified with reference to the mark portion 27. As a result, the X-ray generation device 1 can quickly and accurately specify the target 23 in the target unit T and control the coil unit 9 as deflector to make the electron beam EB incident thereto. Furthermore, since the targets 23 and the mark portions 27 each are arranged with regularity, it is feasible to readily perform movement to the next target 23 and mark portion 27. Therefore, X-rays XR can be efficiently generated.

In the present embodiment, the plurality of targets 23 are arranged in the target unit T. In this configuration, even if one target 23 becomes deteriorated due to heat of the electron beam EB or the like, another target 23 arranged in the same target unit T can be used by deflecting the electron beam EB by the coil unit 9. Therefore, there is no need for replacing the target unit T every time one target 23 becomes deteriorated. As a result, the frequency of replacement of target 23 can be lowered and thus the X-ray generation device 1 can be efficiently used to generate X-rays XR.

In the present embodiment, the length L2 of the mark portions 27 is shorter than the length L1 of the targets 23. For example, if the thickness of the mark portions 27 should be increased (e.g., if it should be increased over 500 nm as large as that of the targets 23), the following problem could arise. Specifically, when the mark portion 27 is irradiated, for example, with the electron beam EB of about 40 keV, 0.3% thereof is converted to X-rays and 99.7% to heat. When it is assumed here that the mark portion 27 is in contact with the substrate 21 only through the bottom face thereof, it is difficult to dissipate the heat to the outside. For this reason, if the mark portion 27 has the large thickness, the heat due to the irradiation with the electron beam EB will accumulate therein, which may cause breakage due to heat. Namely, the target unit T may break, raising a possibility of resulting in making the target unit T unusable. In contrast to it, since in the present embodiment the thickness of the mark portion 27 is smaller than that of target 23, the mark portion 27 can be prevented from breaking due to heat.

In the present embodiment, the irradiation field of the electron beam EB is included in the separation region between the mark portion 27 and target 23. Namely, the mark portion 27 is arranged outside the focused area when the target 23 is irradiated with the electron beam EB to obtain desired X-rays. Because of this, in the X-ray generation device 1, the mark portion 27 is not irradiated with the electron beam EB when the target 23 is irradiated with the electron beam EB. Therefore, the X-ray generation device 1 can prevent the mark portion 27 from affecting X-rays.

The present embodiment has the structure wherein the targets 23 are buried in the holes H of the substrate 21 and the mark portions 27 are arranged as separated so as not to overlap the targets 23 when viewed from the normal direction A. With use of such targets 23, the device can determine the focal spot size of generated X-rays, using the outer size D1 of the targets 23 as a dominant factor, instead of the irradiation field E of the incident electron beam EB, and prevent the mark portions 27 from affecting the X-rays.

On the other hand, as a similar structure, there is a conceivable structure in which, for each large-size target, a region around it except for a desired focal spot size area is covered by an electron shield so as to expose only the focal spot size area to the electron beam (structure in which the target overlaps the electron shield when viewed from the normal direction). However, since the electron shield needs to be configured of such a material that it can certainly shield the target from electrons, X-rays will be generated with a high possibility if the electron beam EB enters the electron shield. Such X-rays result in a noise component, which is undesirable, but, since the focal spot area is determined by the electron shield, the electron shield cannot be located away from the focal spot size area in order to prevent the noise component. Therefore, for obtaining X-rays in a desired focal spot size from the target, it becomes necessary eventually to focus the electron beam into a microscopic area so as to match the irradiation field E itself of the electron beam EB with the focal spot size. For realizing the microscopic area of the irradiation field E of the electron beam EB, the electron beam EB needs to be highly controlled, which is much more difficult than miniaturization of the target. Therefore, it is judged that the foregoing structure cannot fully meet the need for realization of the microscopic area of the X-ray focal spot.

Figure 5:
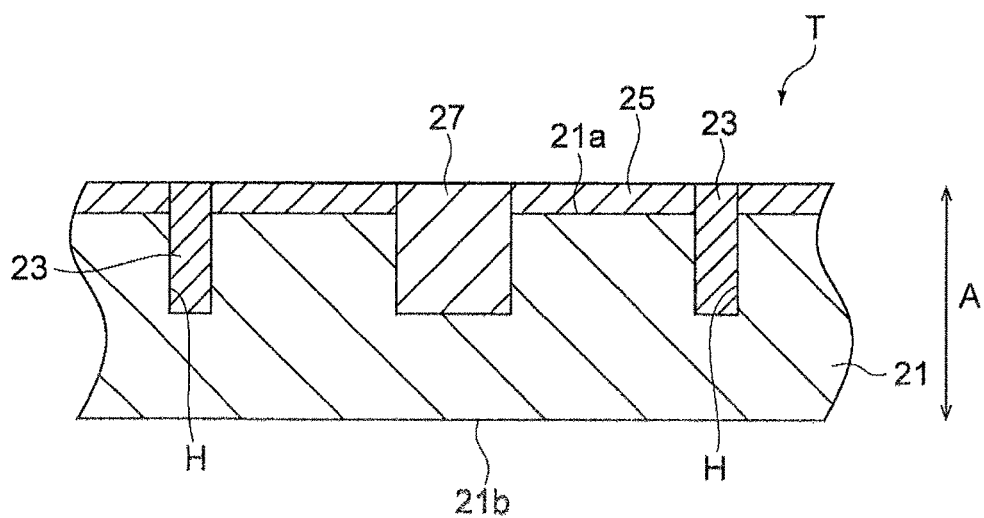
FIG. 5 is a drawing showing a cross-sectional configuration of targets in a direction along a normal direction in the X-ray generation device according to another embodiment.

In addition to the above embodiment, the mark portions 27 may have the configuration as described below. FIG. 5 is a drawing showing a cross-sectional configuration of the targets in the direction along the normal direction in the X-ray generation device according to another embodiment. As shown in FIG. 5, the mark portions 27 are buried in the substrate 21 as the targets 23 are. Furthermore, the mark portions 27 do not only indicate the location information but can also be utilized as targets to make use of X-rays generated with incidence of the electron beam EB thereto. Since the surface area of the mark portion 27 (area on the view from the electron incidence side in the normal direction A to the first and second principal faces 21a, 21b of the substrate 21) is larger than the surface area of the target 23, the X-rays generated with incidence of the electron beam ED to the mark portion 27 can be utilized in cases necessitating the X-rays with a larger focal spot size. Namely, without having to be limited to the configuration wherein the mark portions 27 (second metal members) serve as the members for providing the location information, the X-ray generation device may be configured so that the targets for generation of X-rays can also serve as members for providing the location information.

Figure 6:
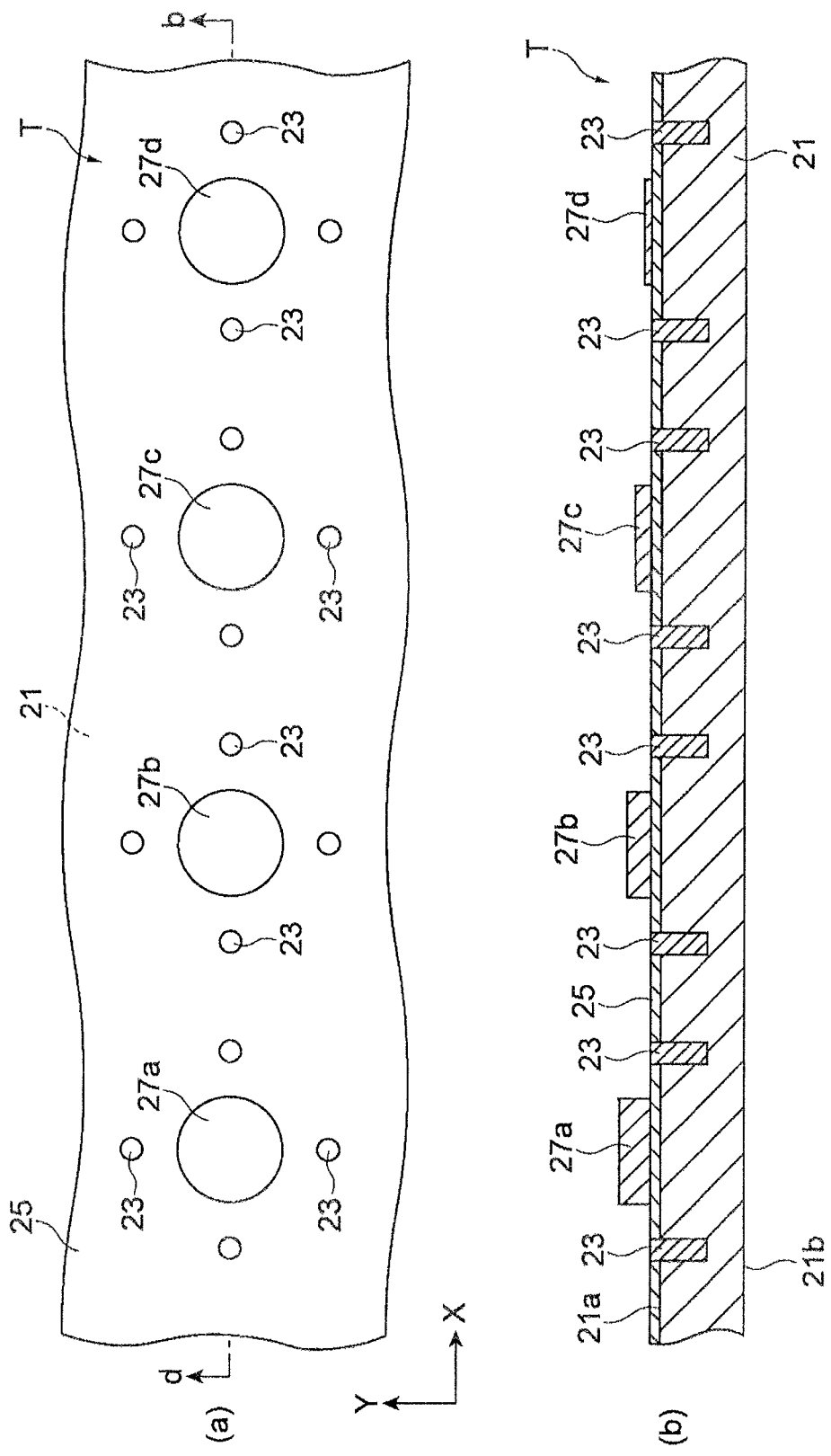
FIG. 6(*a*) is a view of the target unit from the first principal face side of the substrate in the X-ray generation device according to another embodiment, and FIG. 6(*b*) a drawing showing a cross-sectional configuration along the line b-b in FIG. 6(*a*).

FIG. 6(a) is a view of the target unit from the first principal face side of the substrate in the X-ray generation device according to another embodiment and FIG. 6(b) a drawing showing a cross-sectional configuration along the line b-b in FIG. 6(a). As shown in FIG. 6, the mark portions 27a, 27b, 27c, and 27d have their respective lengths (thicknesses) different from each other in the direction along the normal direction A. In detail, the lengths of the mark portions 27a-27d gradually decrease from left to right on the drawing. Of the mark portions 27, the length of the mark portion 27 with the largest length (on the left on the drawing) is smaller than the length of the targets 23. This allows each of the mark portions 27 to be discriminated from the targets 23 and, differences in intensity of reflected electrons therefrom make them discriminable.

For this reason, for example, after all the targets 23 arranged on the circumference of the virtual circle centered at the mark portion 27a are used, the mark portion 27b or 27d different from the mark portion 27a can be readily specified and the targets 23 can be specified based on this mark portion 27b or 27d. Namely, as the mark portions 27a-27d are made discriminable, the search for the targets 23 based on the one-used mark portion 27a-27d is not carried out. Therefore, it becomes feasible to efficiently use all the targets 23 arranged in the target unit T. As a result, the X-ray generation device 1 can efficiently generate X-rays XR. The mark portions 27a-27d need only to have their respective lengths different from each other, and their shape does not have to be limited only to the substantially circular shape.

Figure 7:
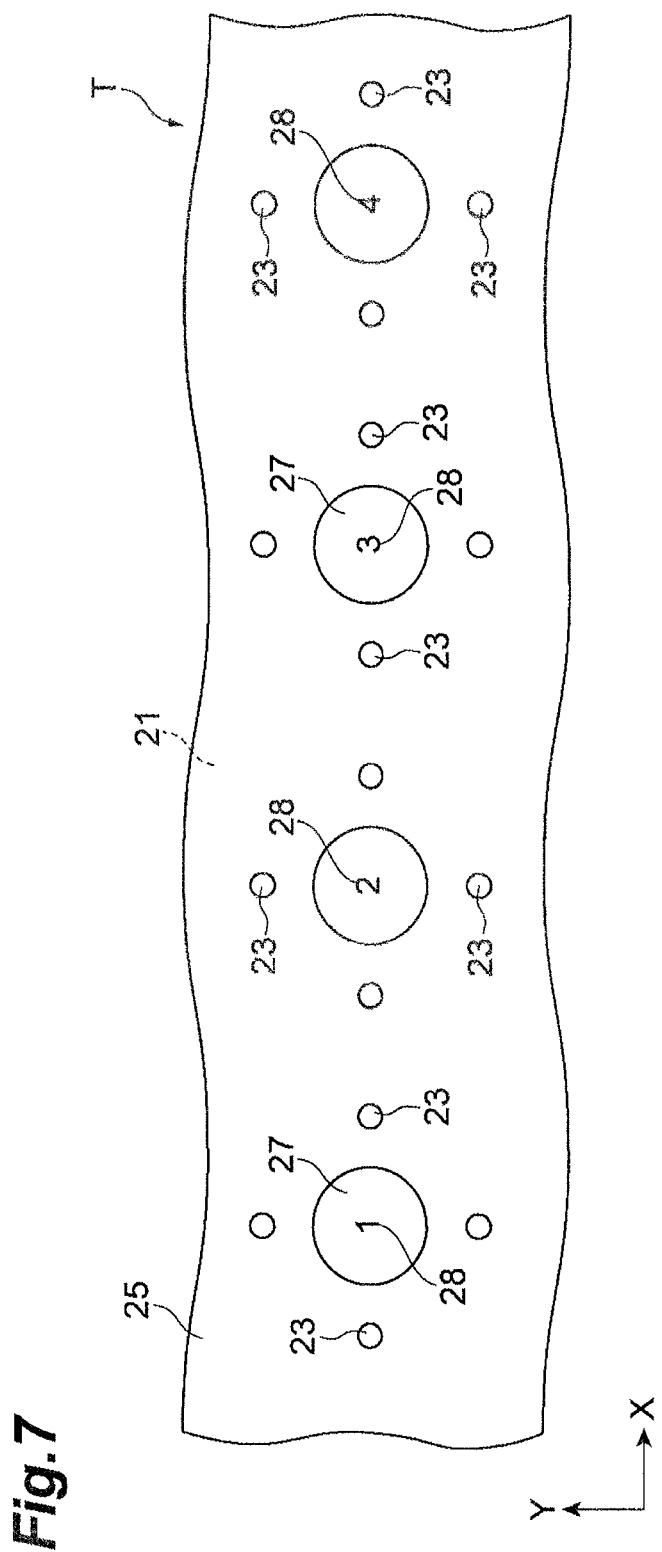
FIG. 7 is a view of the target unit from the first principal face side of the substrate in the X-ray generation device according to another embodiment.

FIG. 7 is a view of the target unit from the first principal face side of the substrate in the X-ray generation device according to another embodiment. As shown in FIG. 7, the mark portions 27 have their respective indications 28. Numerals ("1" to "4" herein) are described as the indications 28. This makes the mark portions 27 discriminable from each other. For this reason, the mark portions 27 can be made discriminable by the indications 28, whereby the search for the targets 23 based on the once-used mark portion 27 is not carried out. Therefore, it becomes feasible to efficiently use all the targets 23 arranged in the target unit T. As a result, the X-ray generation device 1 can efficiently generate X-rays XR.

Second Embodiment

Figure 8:
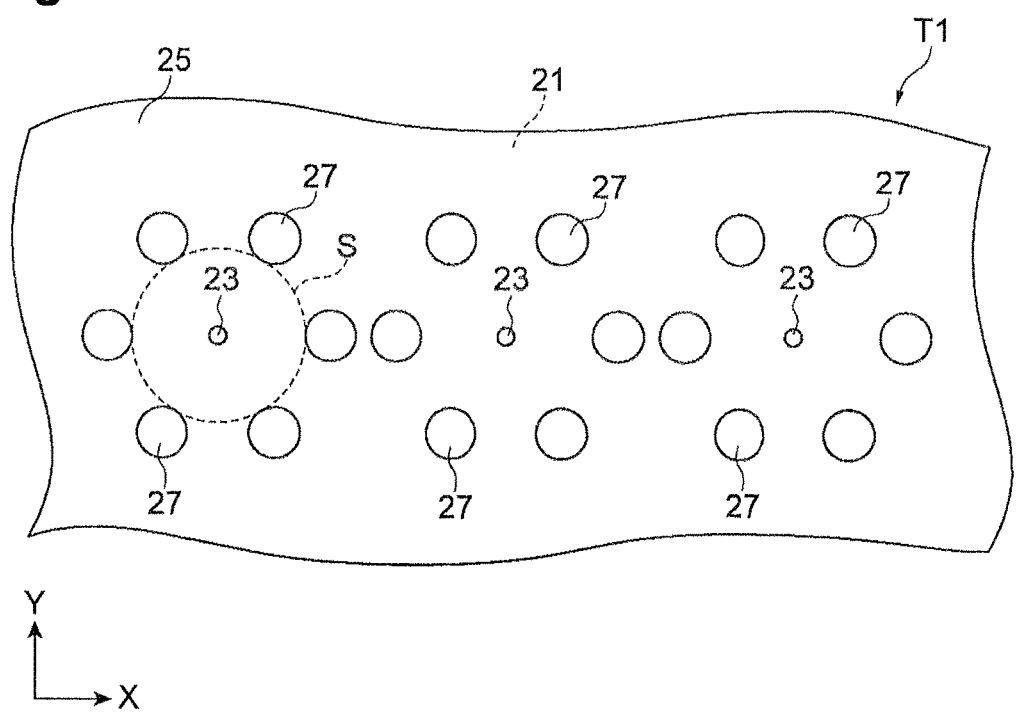
FIG. 8 is a view of the target unit from the first principal face side of the substrate in the X-ray generation device according to the second embodiment.

Next, the second embodiment will be described. FIG. 8 is a view of the target unit from the first principal face side of the substrate in the X-ray generation device according to the second embodiment. As shown in FIG. 8, the target unit T has the substrate 21, targets 23, electroconductive layer 25, and mark portions 27. The target unit T has the same configuration of the substrate 21, targets 23, electroconductive layer 25, and mark portions 27 as that in the first embodiment, but is different in arrangement of the targets 23 and mark portions 27 from that in the first embodiment.

A plurality of (three herein) targets 23 are arranged in the substrate 21 and the arrangement thereof has regularity. Specifically, the targets 23 are arranged at predetermined intervals (equal intervals) on a straight line along the X-direction. The targets 23 are surrounded by the mark portions 27.

The mark portions 27 are arranged as separated so as not to overlap the targets 23, when viewed from the normal direction to the first and second principal faces 21a, 21b of the substrate 21. A plurality of (six herein) mark portions 27 are arranged on the circumference of the virtual circle S centered at the center of each target 23. In the target unit T, a plurality of (three herein) groups are arranged so that each group consists of a plurality of mark portions 27 surrounding the target 23. The mark portions 27 are arranged at their respective locations opposite to each other with the target 23 in between. The neighboring mark portions 27 on the virtual circumference are arranged at equal intervals. Directions in each of which a pair of mark portions 27 are arranged opposite to each other are substantially orthogonal to each other.

The controller 33, when acquiring the location information of the mark portions 27, assumes that the locations where the mark portions 27 are arranged, are on the circumference of a virtual circle S centered at a target 23 and obtains the center of the virtual circle S. After obtaining the center of the virtual circle 5, the controller 33 specifies the location of the target 23, based on the location information of the center and the location information of the targets 23 set in the target unit T and based on the intensity of signal (intensity of reflected electron or absorbed electrons). The controller 33 controls the coil unit 9 as deflector so as to locate the irradiation field of the electron beam EB at the target 23. Alternatively, it may estimate the location of the target 23 from the location information of the mark portions 27 and perform precise re-scanning at a slower speed from a start point of the mark portion 27, thereby specifying the location of the target 23. In the X-ray generation device 1, as described above, the location of the target 23 is specified in the target unit T1 and the target 23 is irradiated with the electron beam EB to generate X-rays with a desired focal spot size.

In the present embodiment, as described above, the plurality of mark portions 27 are arranged on the circumference of the virtual circle S centered at each target 23 in the target unit T1. In the case of this configuration, it is also feasible to specify the location of the target 23 with reference to the mark portions 27. Therefore, since the target unit T1 has the mark portions 27 that are readily detected and that can be discriminated from the targets 23, the target 23 can be quickly and accurately specified in the target unit T1.

Figure 9:
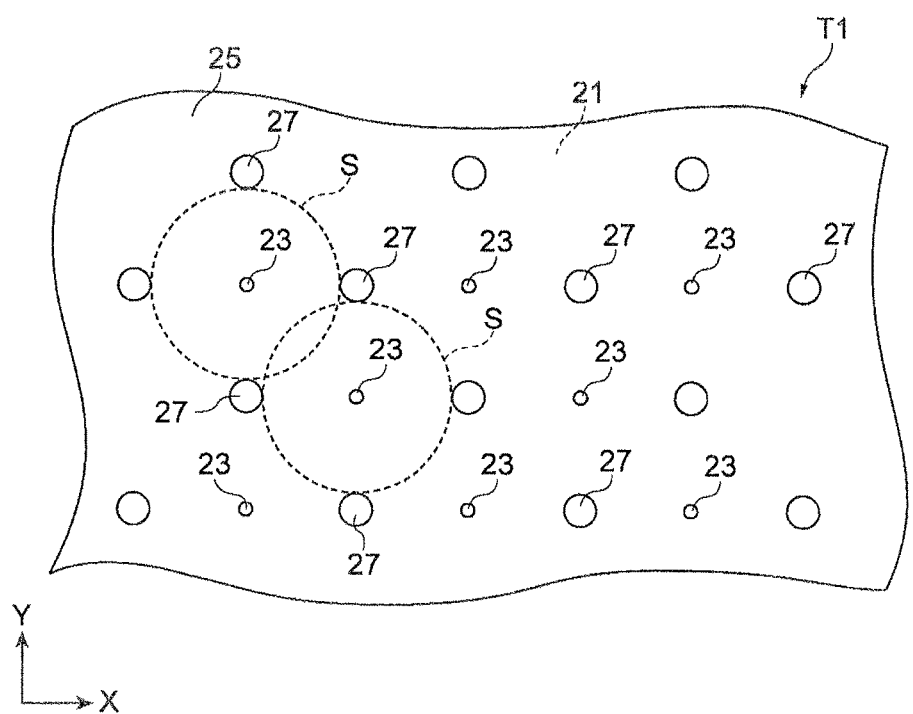
FIG. 9 is a view of the target unit from the first principal face side of the substrate in the X-ray generation device according to another embodiment.

Besides the configuration of the above embodiment, the target unit T1 may have the configuration as shown in FIG. 9. FIG. 9 is a view of the target unit from the first principal face side of the substrate in the X-ray generation device according to another embodiment. In the target unit T1, as shown in FIG. 9, a plurality of (four herein) mark portions 27 are arranged on the virtual circle S centered at each target 23. Each mark portion 27 is located on both of the circumferences of the virtual circle S centered at one target 23 and the virtual circle S centered at another target 23 and functions as a mark portion for each of the targets 23.

Third Embodiment

Figure 10:
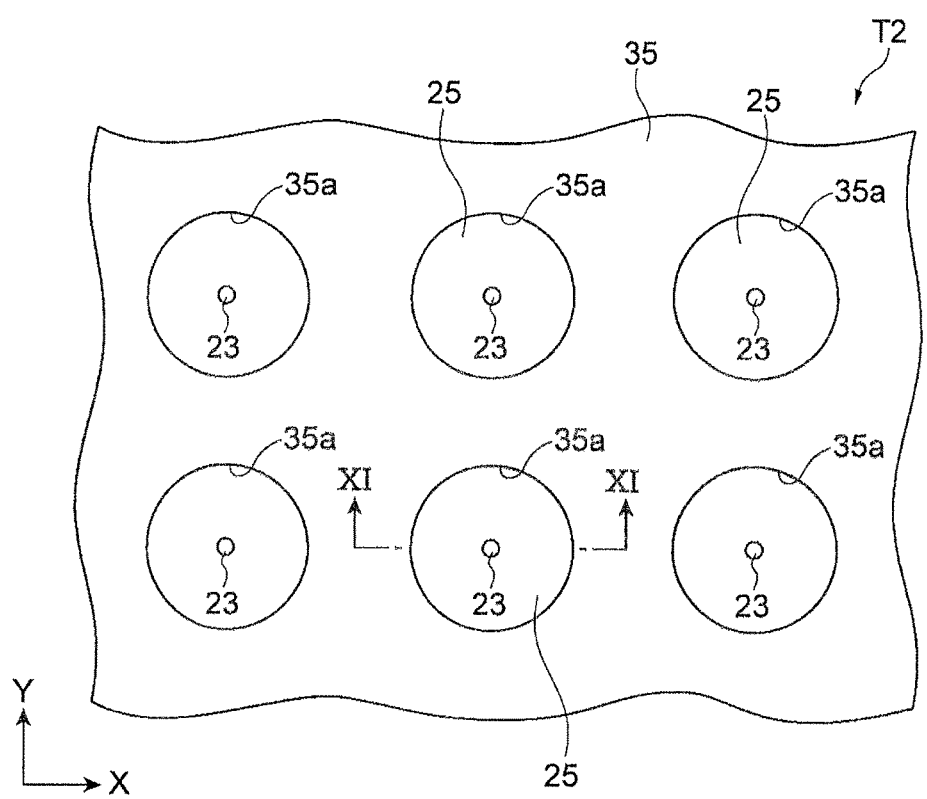
FIG. 10 is a view of the target unit from the first principal face side of the substrate in the X-ray generation device according to the third embodiment.
Figure 11:
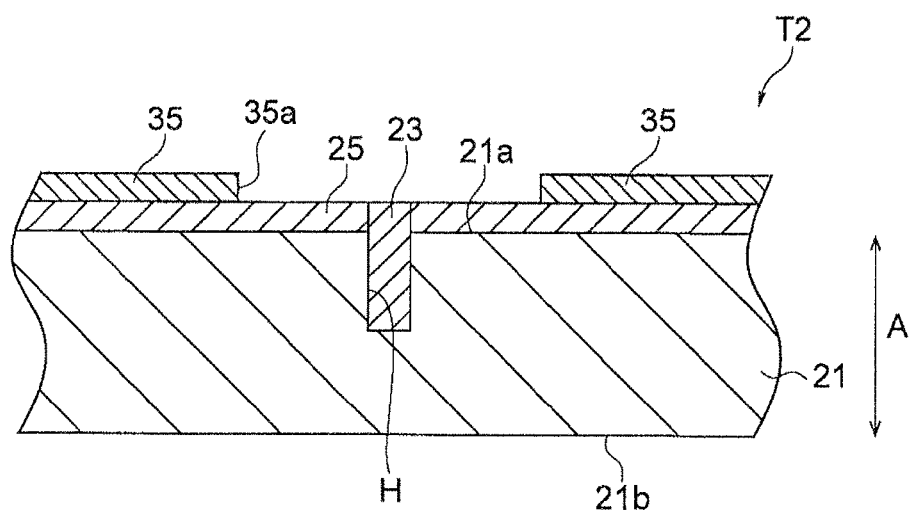
FIG. 11 is a drawing showing a cross-sectional configuration along the line XI-XI in FIG. 10.

Next, the third embodiment will be described. FIG. 10 is a view of the target unit from the first principal face side of the substrate in the third embodiment. FIG. 11 is a drawing showing a cross-sectional configuration along the line X-X line in FIG. 10.

As shown in FIG. 10 and FIG. 11, the target unit T2 has the substrate 21, targets 23, electroconductive layer 25, and mark portion 35. The target unit T2 has the same configuration of the substrate 21, targets 23, and electroconductive layer 25 as that in the first embodiment, but is different in the configuration of the mark portion 35 from that in the first embodiment.

The mark portion 35 is arranged on the electroconductive layer 25. The mark portion 35 is arranged substantially over the entire surface on the first principal face 21a side of the substrate 21 and apertures 35a are formed therein along virtual circles centered at the respective targets 23. The apertures 35a are formed each so as to include one target 23 inside, i.e., one per target 23. The apertures 35a of the mark portion 35 have the inner diameter of approximately 10 to 50 µm.

For specifying a target 23 in the foregoing target unit T2, the controller 33 searches the surface for an aperture 35a of the mark portion 35 and detects the edge (open end) of the aperture 35a. When detecting the edge of the aperture 35a, the controller 33 determines the center of the aperture 35a. After determining the center of the aperture 35a, the controller 33 specifies the location of the target 23, based on the location information of the center and the location information of the targets 23 set in the target unit T2 and based on the intensity of reflected electrons (absorbed electrons). Namely, in the present embodiment, the apertures 35a and the edges (open ends) of the apertures 35a, of the mark portion 35, have a predetermined location relationship with the targets 23.

Although the above embodiment was described with the example of the configuration wherein the electroconductive layer 25 was arranged on the first principal face 21a of the substrate 21 and wherein the mark portion 35 was arranged on the electroconductive layer 25, the electroconductive layer 25 may be arranged on the first principal face 21a of the substrate 21, the targets 23, and the mark portion 35. Namely, the mark portion 35 may be arranged directly on the first principal face 21a of the substrate 21. In the configuration wherein the mark portion 35 covers substantially the entire area of the first principal face 21a of the substrate 21, the electroconductive layer 25 may be configured to cover only the apertures 35a and, in that case, the electron incidence faces of the targets 23 may be exposed.

In the above embodiment the apertures 35a are of the substantially circular shape but the apertures may be of a polygonal shape.

Fourth Embodiment

Figure 12:
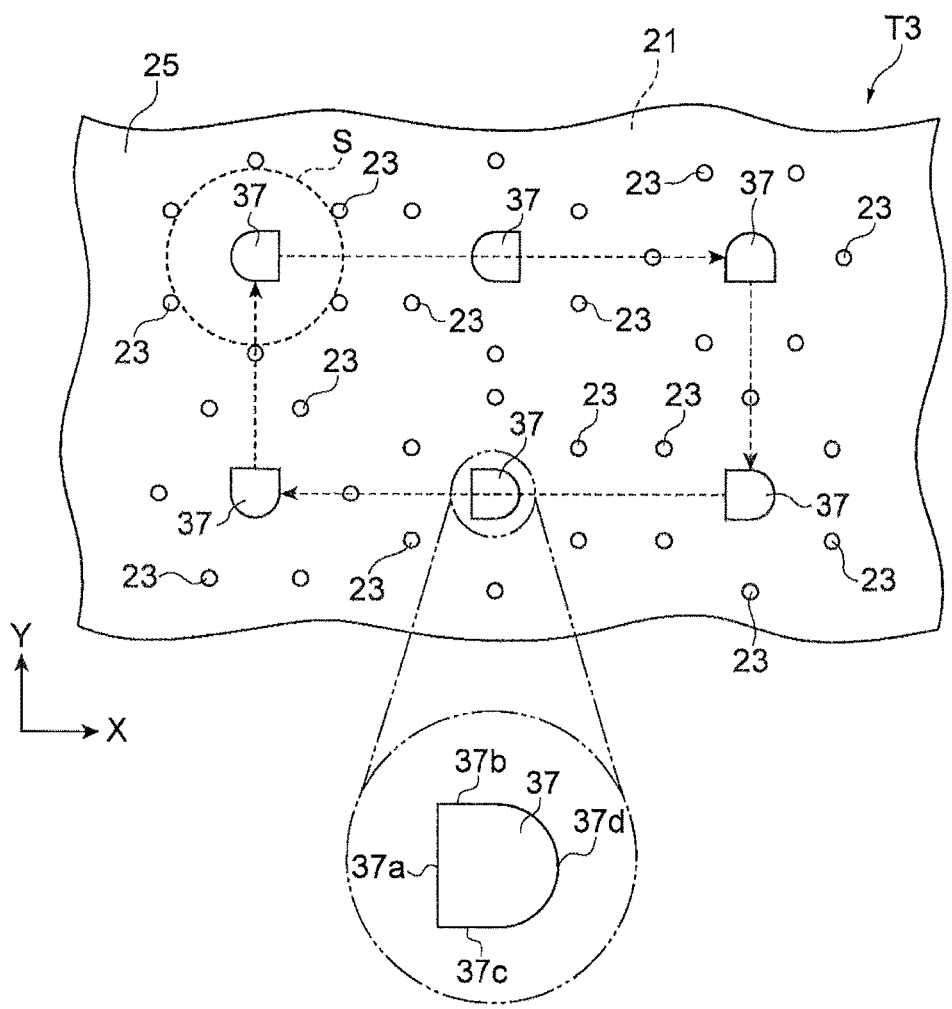
FIG. 12 is a view of the target unit from the first principal face side of the substrate in the X-ray generation device according to the fourth embodiment.

Next, the fourth embodiment will be described. FIG. 12 is a view of the target unit from the first principal face side of the substrate in the X-ray generation device according to the fourth embodiment. As shown in FIG. 12, the target unit T3 has the substrate 21, targets 23, electroconductive layer 25, and mark portions 37. The configuration of the substrate 21, targets 23, and electroconductive layer 25 is the same as in the first embodiment and the configuration of the mark portions 37 is different from that in the first embodiment.

A plurality of (six herein) targets 23 are arranged on the circumference of the virtual circle S centered at the center of each mark portion 37. In the target unit 13, a plurality of (six herein) groups are arranged so that each group consists of a plurality of targets 23 surrounding the mark portion 37.

A plurality of (six herein) mark portions 37 are arranged. The mark portions 37 are arranged with a predetermined location relationship with the targets 23. Specifically, each of the mark portions 37 is located at the center of the virtual circle S on the circumference of which the targets 23 are arranged. In regard to only the mark portions 37, the mark portions 37 are arranged at predetermined intervals (equal intervals) on a straight line along the X-direction and arranged at predetermined intervals (equal intervals) on a straight line along the Y-direction.

The mark portions 37 are of an arch shape. In detail, each mark portion 37 has a smooth flat edge 37a, a pair of side edges 37b, 37c extending in parallel to each other from the two ends of this flat edge 37a, and a curved edge 37d of an arcuate shape (semicircular shape) connecting the ends of the pair of side edges 37b, 37c, and is thus of a so-called shell shape. Because of this shape, the mark portions 37 have directionality. Namely, the mark portions 37, for example different from the mark portions of the circular shape, are uniquely set in a certain direction by a way of arrangement thereof making use of the difference of the shapes of the respective edges. For example, as shown in FIG. 12, the mark portions 37 are arranged so that the mark portions 37 are located in directions in which the flat edges 37a face. Namely, when the mark portions 37 are classified into first mark portions 37 and second mark portions 37, each first mark portion 37 has the location information of the second mark portion adjacent thereto. In this case of the mark portions 37, the curved edges 37d, instead of the flat edges 37a, may be arranged so as to indicate the locations of the other mark portions 37.

In the target unit T3, the surface is searched for a mark portion 37 along the directions of arrows in the drawing. Namely, the controller 33 specifies the targets 23, based on a certain mark portion 37, and when all the targets 23 arranged on the circumference of the virtual circle S of the mark portion 37 are used, it acquires the next mark portion 37 from the direction of the mark portion 37 (direction in which the flat edge 37a faces) and controls the coil unit 9 to detect the next mark portion 37.

In the present embodiment, as described above, the mark portions 37 are of the unique shape, with directionality. In this configuration, after all the targets 23 arranged on the circumference of the virtual circle S centered at a certain mark portion 37 are used, the controller goes back again to the mark portion 37 located at the center of the same virtual circle S, whereby it can acquire the direction in which the next mark portion 37 is arranged. Therefore, movement to the next mark portion 37 can be readily performed and the next mark portion 37 can be efficiently detected. In addition, since a mark portion 37 can be certainly detected, it becomes feasible to use all the targets 23 arranged around the mark portion 37. As a result, the X-ray generation device 1 can efficiently generate X-rays XR.

Figure 13:
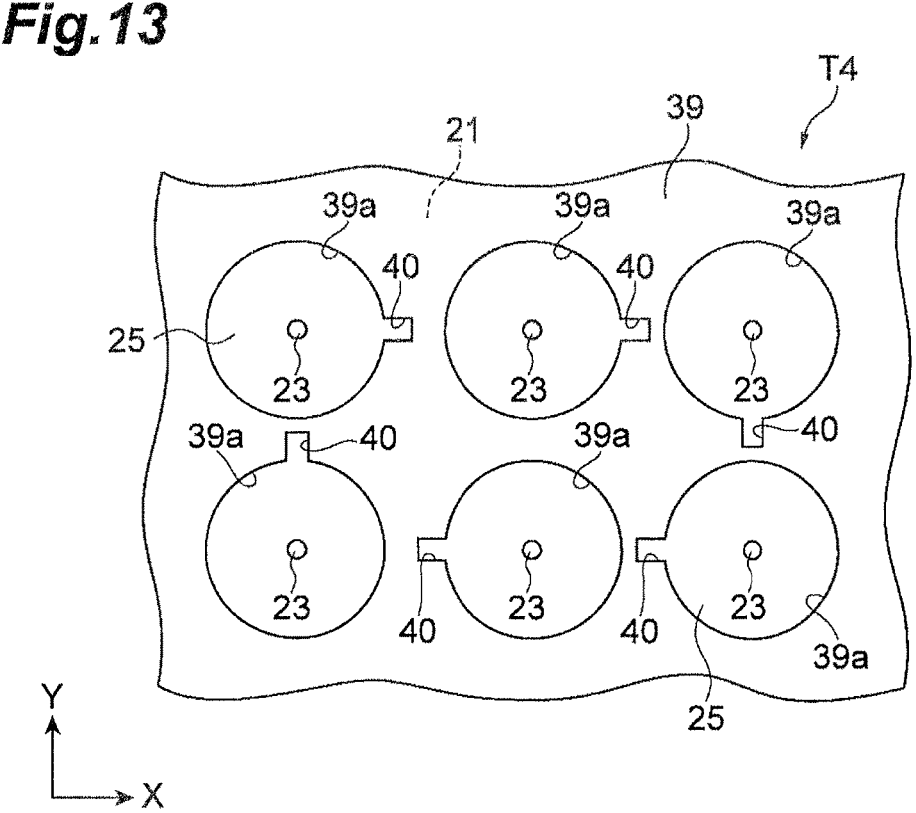
FIG. 13 is a view of the target unit from the first principal face side of the substrate in the X-ray generation device according to another embodiment.

The above embodiment was described with the example of the configuration wherein the shape of the mark portions 37 was the shell shape so that the mark portions 37 had directionality, but the shape of the mark portions with directionality does not have to be limited only to this. FIG. 13 is a view of the target unit from the first principal face side of the substrate in the X-ray generation device according to another embodiment. As shown in FIG. 13, the target unit T4 has the substrate 21, targets 23, electroconductive layer 25, and mark portion 39. The target unit T4 has the same configuration of the substrate 21, targets 23, and electroconductive layer 25 as that in the second embodiment but is different in the configuration of the mark portion 39 from that in the second embodiment.

The mark portion 39 is arranged on the electroconductive layer 25. The mark portion 39 is arranged substantially over the entire surface on the first principal face 21a side of the substrate 21 and apertures 39a are formed therein along virtual circles centered at the respective targets 23. Namely, in the present embodiment, the apertures 39a and the edges (open ends) of the apertures 39a, of the mark portion 39, have a predetermined location relationship with the targets 23. Each aperture 39a has a depression 40 formed in a concave shape from the edge of the aperture 39a. The depression 40 is arranged as oriented in a direction in which the mark portion 39 adjacent thereto is arranged. Because of this, the mark portions 39 have directionality. Namely, by detecting the depression 40 provided in the aperture 39a of the mark portion 39, the direction in which the next mark portion 39 is arranged can be acquired. It is noted that, without having to be limited only to the concave shape, it is also possible to adopt a convex shape formed so as to project from the edge of the aperture 39a.

Figure 14:
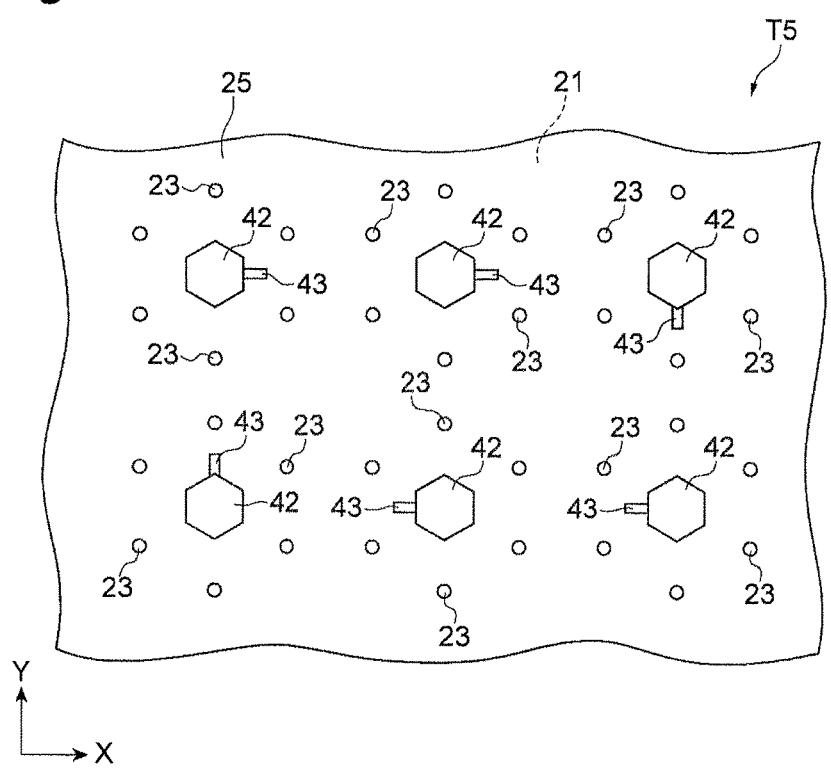
FIG. 14 is a view of the target unit from the first principal face side of the substrate in the X-ray generation device according to another embodiment.

FIG. 14 is a view of the target unit from the first principal face side of the substrate in the X-ray generation device according to another embodiment. As shown in FIG. 14, the target unit T5 has the substrate 21, targets 23, electroconductive layer 25, and mark portions 42. The target unit T5 has the same configuration of the substrate 21, targets 23, and electroconductive layer 25 as that in the first embodiment but is different in the configuration of the mark portions 42 from that in the first embodiment.

The mark portions 42 are of a polygonal shape and are of a hexagonal shape herein. Each of the apexes (vertices) of the mark portions 42 is oriented in a direction in which a target 23 is arranged. In other words, the targets 23 are arranged on extension lines from the respective apexes of each mark portion 42. Namely, the mark portions 42 have the configuration to indicate the directions in which the targets 23 are arranged. Because of this configuration, when acquiring the location information of a mark portion 42, the X-ray generation device 1 scans the target unit in a direction of a vertex of the mark portion 42, whereby it can quickly and accurately specify a target 23. Furthermore, each mark portion 42 has a projection 43 formed so as to project from one side of the mark portion 42. The projection 43 is arranged as oriented in a direction in which the mark portion 42 adjacent thereto is arranged. Because of this, the mark portions 42 have directionality. Namely, by detecting the projection 43 of the mark portion 42, the direction in which the next mark portion 42 is arranged can be acquired. Without having to be limited to the projecting shape, it is also possible to adopt a concave shape formed so as to be depressed from one side of the mark portion 42.

Figure 15:
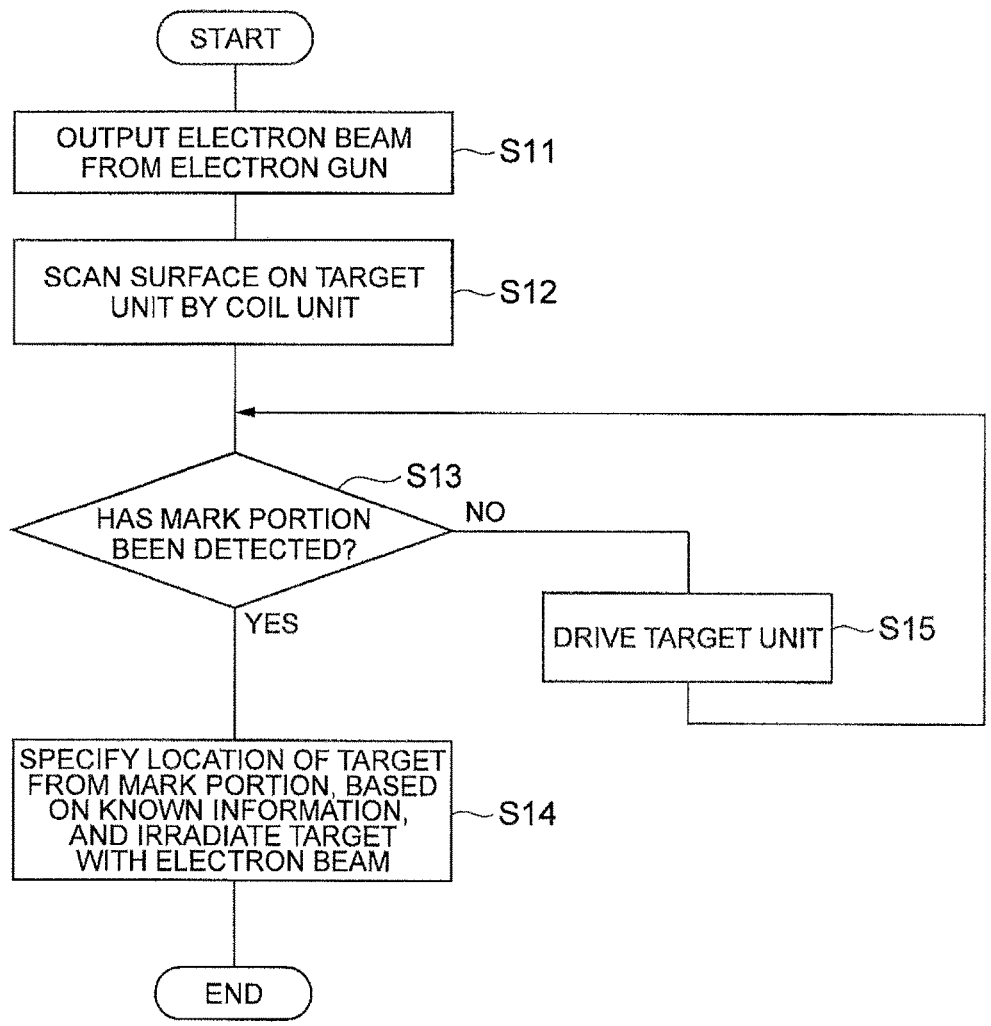
FIG. 15 is a flowchart showing a method to specify a target.

Next, a method to specify a target 23 in FIG. 14 will be described. FIG. 15 is a flowchart showing the target specifying method.

As shown in FIG. 15, first, the electron gun 3 outputs the electron beam EB (step S11). Subsequently, the controller 33 controls the coil unit 9 as deflector to scan the surface on the target unit T5 with the electron beam EB (step S12). Then the device searches the surface for a mark portion 42 while monitoring the intensity of reflected electrons detected by the reflected electron detector 31 (or absorbed electrons detected by the current detector 32), and whether a mark portion 42 has been detected is determined (step S13). When it is determined that a mark portion 42 has been detected, the flow goes to step S14. On the other hand, when no mark portion 42 has been detected, the target unit T is moved by the XY stage 34 (step S15).

The controller 33, when acquiring the location information of the mark portion 42, assumes that a target 23 is arranged on an extension line from a vertex of the mark portion 42, the controller 33 specifies the location of the target 23, based on the location information on the extension line from the vertex and the location information of the targets 23 set in the target unit T5 and based on the intensity of signal (intensity of reflected electron or absorbed electrons), and then the controller 33 controls the coil unit 9 as deflector so as to locate the irradiation field of the electron beam EB at the target 23 (step S14). In the X-ray generation device 1, as described above, the location of the target 23 is specified in the target unit T5 and the target 23 is irradiated with the electron beam EB to generate X-rays XR with a desired focal spot size. When the targets 23 become deteriorated (or used up), the electron beam EB is moved to the next mark portion 42, based on the projection 43 of the mark portion 42, and X-rays XR are generated by the same procedure as above.

In the above embodiment, the directions in which the targets 23 are arranged are indicated by the shape of the mark portions 42, but each mark portion 42 may be provided with an indication (e.g., an arrow or the like) indicative of a direction in which each target 23 is arranged.

Fifth Embodiment

Figure 16:
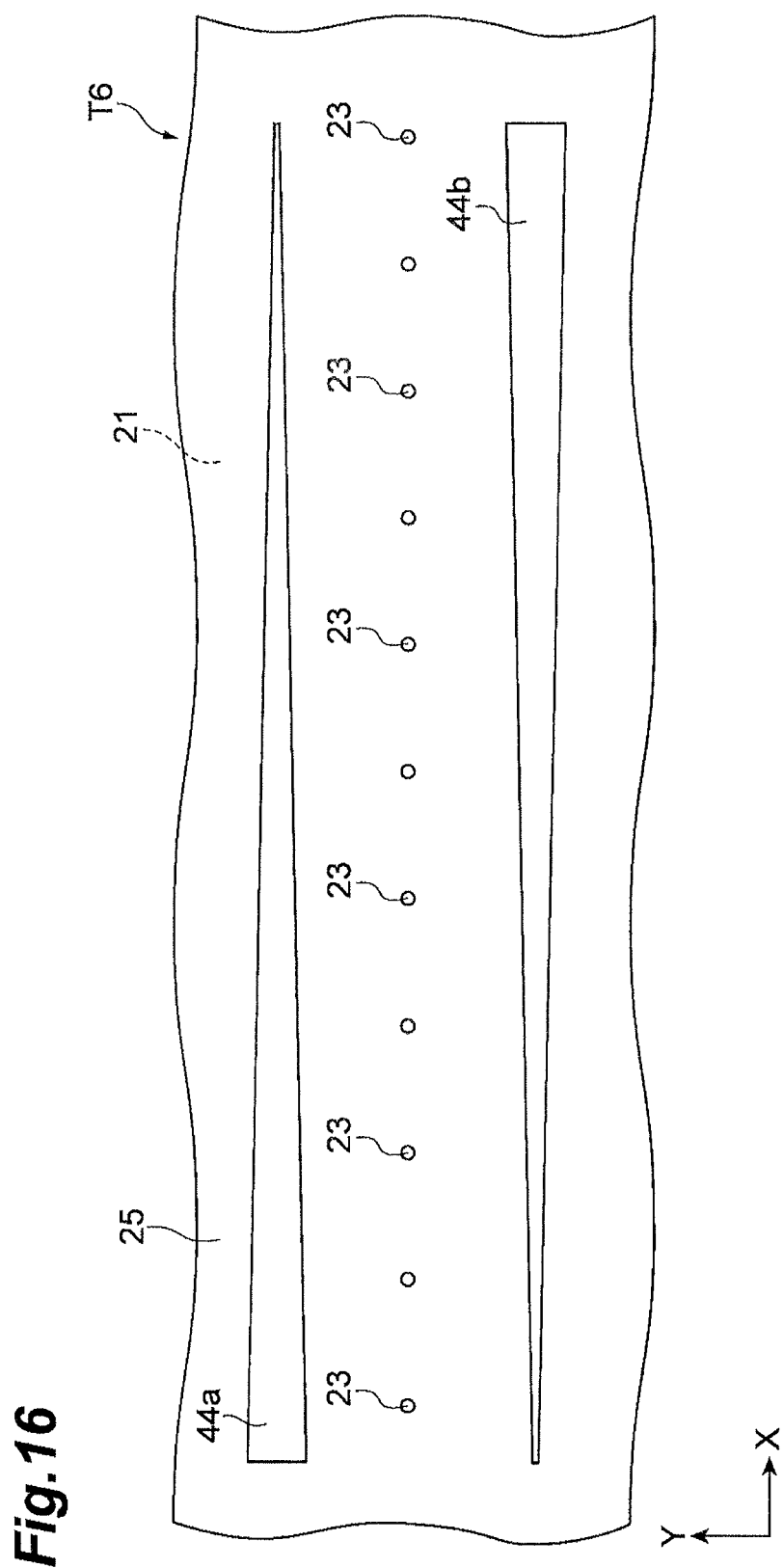
FIG. 16 is a view of the target unit from the first principal face side of the substrate in the X-ray generation device according to the fifth embodiment.

Next, the fifth embodiment will be described. FIG. 16 is a view of the target unit from the first principal face side of the substrate in the X-ray generation device according to the fifth embodiment. As shown in FIG. 16, the target unit T6 has the substrate 21, targets 23, electroconductive layer 25, and mark portions 44a, 44b. The configuration of the substrate 21, targets 23, and electroconductive layer 25 is the same as in the first embodiment and the configuration of the mark portions 44a, 44b is different from that in the first embodiment.

A plurality of (eleven herein) targets 23 are arranged in the substrate 21 and the arrangement thereof has regularity. Specifically, the targets 23 are arranged at predetermined intervals (equal intervals) on a straight line along the X-direction.

The mark portions 44a, 44b are arranged as separated with the targets 23 in between. Each of the mark portions 44a, 44b extends along the arrangement direction (X-direction) of the targets 23. In other words, the targets 23 are arranged along the extending direction of the mark portions 44a, 44b. Each of the mark portions 44a, 44b is of a taper shape. Specifically, the mark portion 44a is of a taper shape as tapered from one end side (the left on the drawing) to the other end side (the right on the drawing). The mark portion 44b is of a taper shape as tapered from the other end side (the right on the drawing) to the one end side (the left on the drawing).

In the present embodiment, as described above, the targets 23 are arranged along the extending direction of the mark portions 44a, 44b. Since this makes the region where the targets 23 are arranged, clear in the target unit T6, the targets 23 can be efficiently specified. Since the mark portions 44a, 44b are of the taper shape, the area thereof located inside the range of the irradiation field of the electron beam EB including a certain target 23 varies target 23 by target 23. In other words, it can also be said that the mark portions 44a, 44b are assemblies of mark portions with a predetermined location relationship corresponding to each target 23. For this reason, the intensity of reflected electrons or absorbed electrons by the mark portions 44a, 44b varies with movement of the electron beam EB and thus the location of each target 23 can be readily specified, based on the location information of the mark portions 44a, 44b, the location information of the targets 23 set in the target unit T6, and the intensity of signal (intensity of reflected electrons or absorbed electrons). Therefore, X-rays XR can be efficiently generated. It is noted that the same effect can also be achieved by only either one of the mark portions 44a, 44b.

Sixth Embodiment

Figure 17:
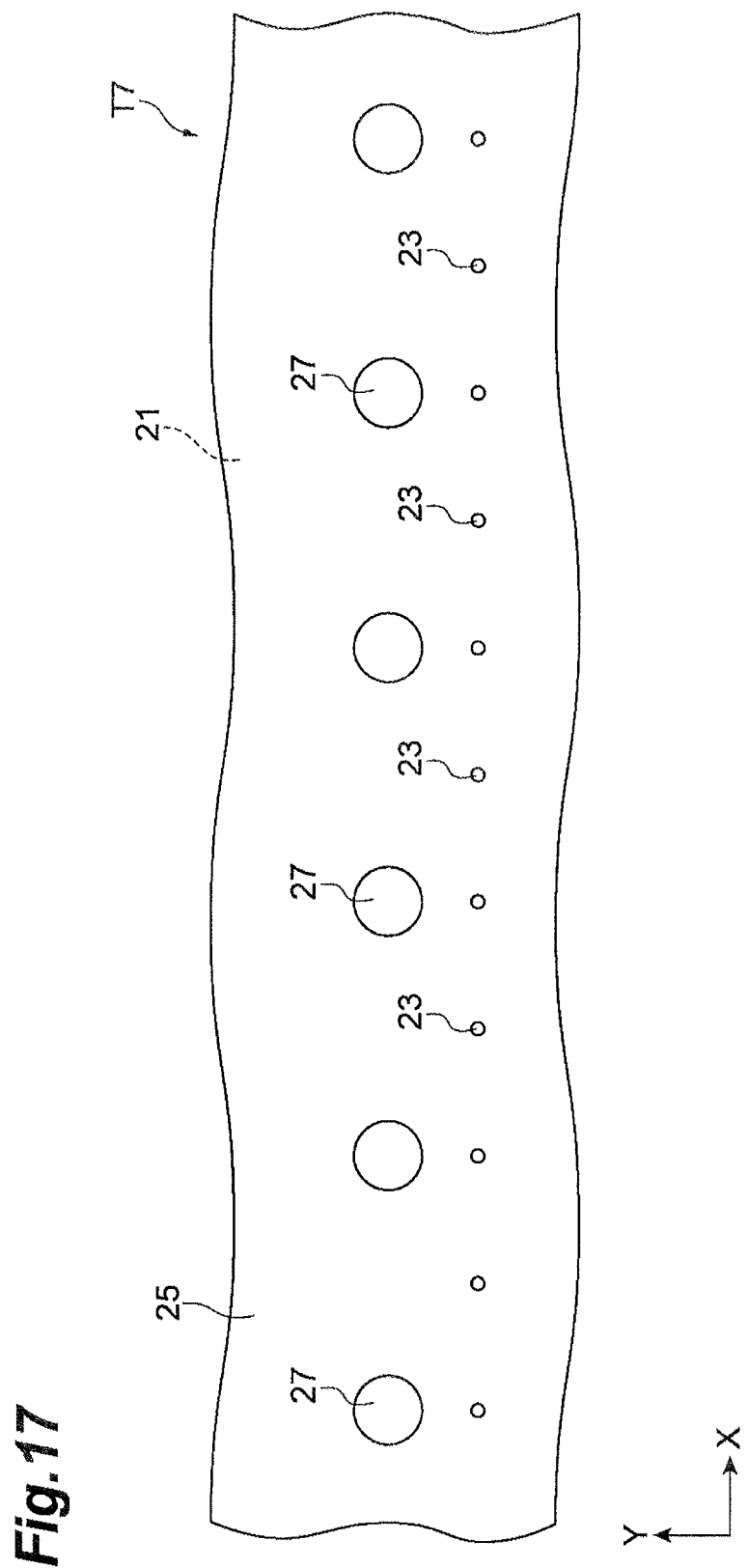
FIG. 17 is a view of the target unit from the first principal face side of the substrate in the X-ray generation device according to the sixth embodiment.

Next, the sixth embodiment will be described. FIG. 17 is a view of the target unit from the first principal face side of the substrate in the X-ray generation device according to the sixth embodiment. As shown in FIG. 17, the target unit T7 has the substrate 21, targets 23, electroconductive layer 25, and mark portions 27. The configuration of the substrate 21, targets 23, electroconductive layer 25, and mark portions 27 is the same as in the first embodiment and the arrangement of the mark portions 27 is different from that in the first embodiment.

A plurality of (eleven herein) targets 23 are arranged in the substrate 21 and the arrangement thereof has regularity. Specifically, the targets 23 are arranged at predetermined intervals (equal intervals) on a straight line along the X-direction.

A plurality of (six herein) mark portions 27 are arranged along the arrangement direction of the targets 23. In other words, the targets 23 are arranged along the arrangement direction of the mark portions 27. The mark portions 27 are arranged at predetermined intervals (equal intervals) on a straight line along the X-direction.

In the present embodiment, as described above, the targets 23 are arranged along the arrangement direction of the mark portions 27. Since this makes the region where the targets 23 are arranged, clear in the target unit T7, the targets 23 can be efficiently specified. Therefore, X-rays XR can be efficiently generated.

Seventh Embodiment

Figure 18:
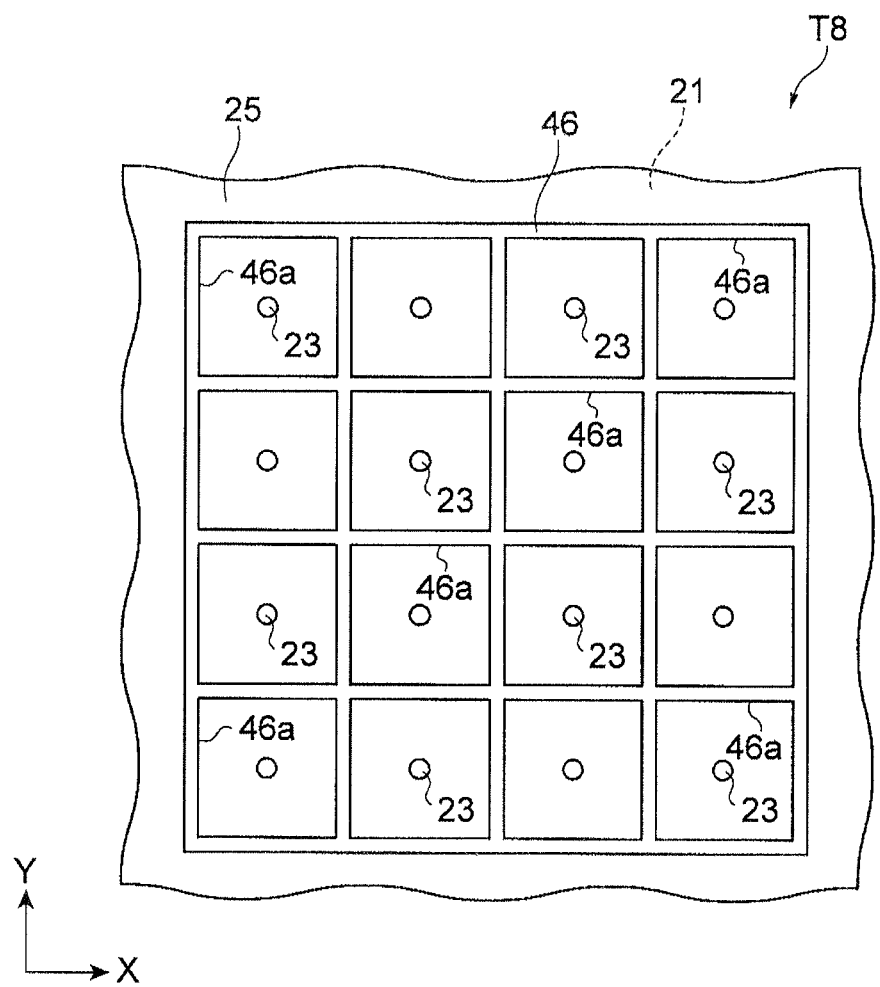
FIG. 18 is a view of the target unit from the first principal face side of the substrate in the X-ray generation device according to the seventh embodiment.

Next, the seventh embodiment will be described. FIG. 18 is a view of the target unit from the first principal face side of the substrate in the X-ray generation device according to the seventh embodiment. As shown in FIG. 18, the target unit T8 has the substrate 21, targets 23, electroconductive layer 25, and mark portion 46. The target unit T8 has the same configuration of the substrate 21, targets 23, and electroconductive layer 25 as that in the first embodiment but is different in the configuration of the mark portion 46 from that in the first embodiment.

The mark portion 46 is arranged on the electroconductive layer 25. The mark portion 46 is of a grid shape, when viewed from the first principal face 21a side of the substrate 21, and has a plurality of apertures 46a. In detail, the targets 23 are surrounded by the mark portion 46 and each aperture 46a is formed so as to include one target 23 at the center thereof; that is, the apertures 46a are formed corresponding to the respective targets 23. The separation distance between mark portion 46 and target 23 is, for example, approximately from 10 to 50 μm. The width of the mark portion 46 is, for example, from 3 to 10 μm.

For specifying a target 23 in the foregoing target unit T8, the controller 33, when acquiring the location information of the mark portion 46, detects the edge of an aperture 46a of the mark portion 46. After detecting the edge of the aperture 46a of the mark portion 46, the controller 33 determines the center of the mark portion 46. After determining the center of the mark portion 46, the controller 33 specifies the location of the target 23, based on the location information of the center and the location information of the targets 23 set in the target unit T8 and based on the intensity of signal (intensity of reflected electrons or absorbed electrons). Namely, in the present embodiment, the apertures 46a and the edges (open ends) of the apertures 46a, of the mark portion 46, have a predetermined location relationship with the targets 23.

Figure 19:
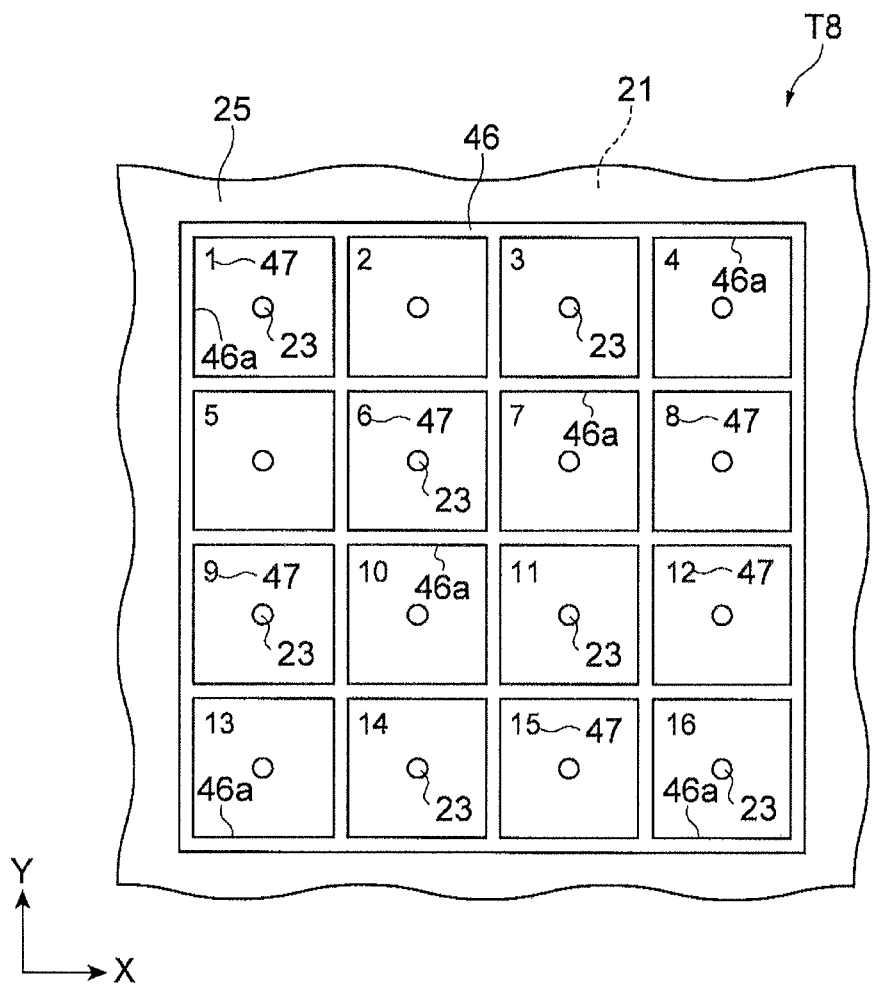
FIG. 19 is a view of the target unit from the first principal face side of the substrate in the X-ray generation device according to another embodiment.

In addition to the above embodiment, as shown in FIG. 19, the target unit T8 may be provided with indications 47. In detail, the indications 47 are provided inside the respective apertures 46a of the mark portion 46. Numerals ("1" to "16" herein) are described as the indications 47. This makes each of the apertures discriminable from the others. For this reason, all the targets 23 arranged in the target unit T8 can be efficiently used based on the indications 47. As a result, the X-ray generation device 1 can efficiently generate X-rays XR.

Eighth Embodiment

Figure 20:
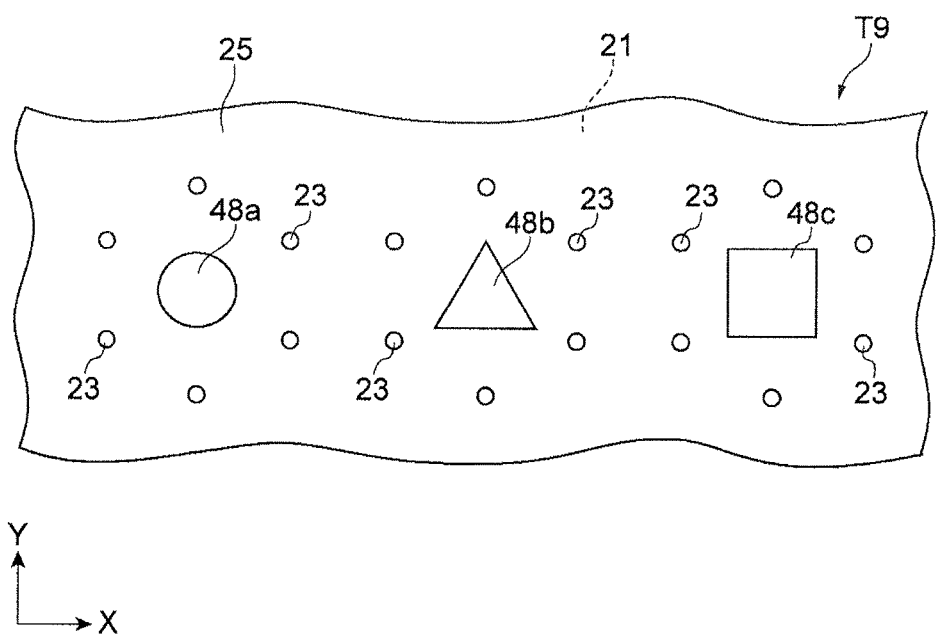
FIG. 20 is a view of the target unit from the first principal face side of the substrate in the X-ray generation device according to the eighth embodiment.

Next, the eighth embodiment will be described. FIG. 20 is a view of the target unit from the first principal face side of the substrate in the X-ray generation device according to the eighth embodiment. As shown in FIG. 20, the target unit T9 has the substrate 21, targets 23, electroconductive layer 25, and mark portions 48a, 48b, and 48c. The target unit T9 has the same configuration of the substrate 21, targets 23, and electroconductive layer 25 as that in the first embodiment but is different in the configuration of the mark portions 48a-48c from that in the first embodiment.

The mark portions 48a-48c are different in shape from each other. Specifically, when viewed from the normal direction to the first and second principal faces 21a, 21b of the substrate 21, the mark portion 48a is of a circular shape, the mark portion 48b of a triangular shape, and the mark portion 48c of a rectangular shape. This makes each of the mark portions 48a-48c discriminable from the others.

In the present embodiment, as described above, the shapes of the mark portions 48a-48c are different from each other, thereby to make the mark portions 48a-48c discriminable.

For this reason, for example, after all the targets 23 arranged on the circumference of the virtual circle centered at the mark portion 48a are used, it is feasible to readily specify the mark portion 48b or 48c different from the mark portion 48a and to specify the targets 23, based on this mark portion 48b or 48c. Namely, as the mark portions 48a-48c are made discriminable, the device does not have to perform the search for the targets 23 based on the once-used mark portion 48a-48c. Therefore, it becomes feasible to efficiently use all the targets 23 arranged in the target unit T9. As a result, the X-ray generation device 1 can efficiently generate X-rays XR.

Ninth Embodiment

Figure 21:
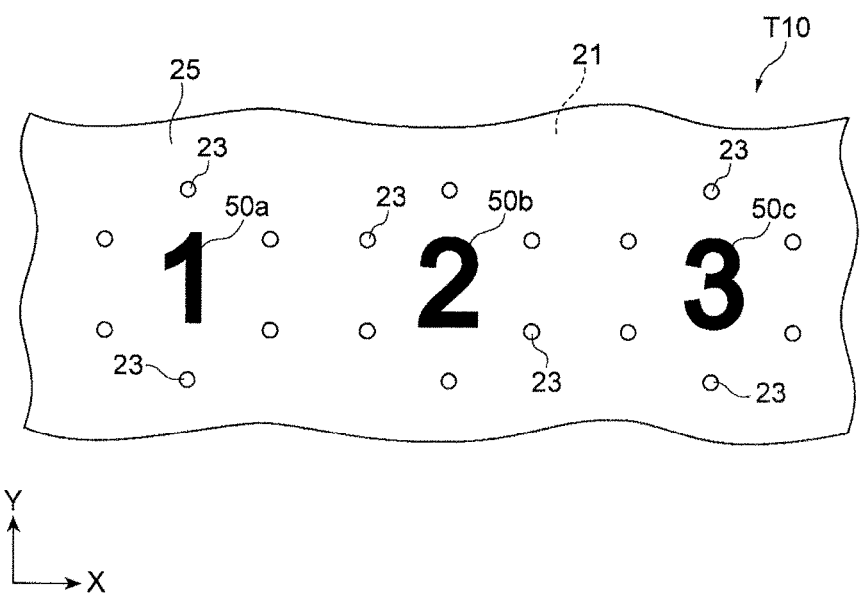
FIG. 21 is a view of the target unit from the first principal face side of the substrate in the X-ray generation device according to the ninth embodiment.

Next, the ninth embodiment will be described. FIG. 21 is a view of the target unit from the first principal face side of the substrate in the X-ray generation device according to the ninth embodiment. As shown in FIG. 21, the target unit T10 has the substrate 21, targets 23, electroconductive layer 25, and mark portions 50a, 50b, and 50c. The target unit T10 has the same configuration of the substrate 21, targets 23, and electroconductive layer 25 as that in the first embodiment but is different in the configuration of the mark portions 50a-50c from that in the first embodiment.

The mark portions 50a-50c are characters. Specifically, in the present embodiment, the mark portions 50a-50c are numerals and are described as "1," "2," and "3," respectively. This makes each of the mark portions 50a-50c discriminable from the others.

In the present embodiment, as described above, the mark portions 50a-50c are expressed by numerical notation to make each of the mark portions 50a-50c discriminable. For this reason, for example, after all the targets 23 arranged on the circumference of the virtual circle centered at the mark portion 50a are used, it is feasible to readily specify the mark portion 50b or 50c different from the mark portion 50a and to specify the targets 23, based on this mark portion 50b or 50c. Namely, as the mark portions 50a-50c are made discriminable, the device does not have to perform the search for the targets 23 based on the once-used mark portion 50a-50c. Therefore, it becomes feasible to efficiently use all the targets 23 arranged in the target unit T10. As a result, the X-ray generation device 1 can efficiently generate X-rays XR.

The preferred embodiments of the X-ray generation device of the present invention have been described above, but it should be noted that the present invention does not always have to be limited only to the above-described embodiments and can be varied in many ways without departing from the spirit and scope of the invention.

REFERENCE SIGNS LIST

1 X-ray generation device; 3 electron gun; 5 tubular portion (housing); 9 coil unit (deflector); 11 electron passage; 21 substrate; 23 targets (first metal members); 27, 27a-27c, 35, 37, 39, 42, 44a, 44b, 46, 48a-48c, or 50a-50c mark portions (second metal members); 31 reflected electron detector (incident signal acquisition unit); 32 current detector (incident signal acquisition unit); EB electron beam; T, T1, T2, T3, T4, T5, T6, T7, T8, T9, or T10 target unit.

The invention claimed is:

1. An X-ray generation device comprising:
an electron gun for emitting an electron beam;
a target unit having a target buried in a substrate having principal faces opposed to each other;
a housing at one end side of which the target unit is arranged and at the other end side opposed to the one end side of which the electron gun is arranged, the housing having an electron passage for the electron beam to pass;
a deflector for deflecting the electron beam passing in the electron passage to enable scanning on the target unit;
a signal acquisition unit for acquiring an incident signal generated from scanning the target unit with the electron beam; and
a control unit for controlling the deflector, based on the incident signal acquired by the signal acquisition unit,
wherein the target unit comprises:
the substrate comprising an electrical insulating material having X-ray permeability
a plurality of first metal members buried in the substrate and serving as the target; and
one or more second metal members, the one or more second metal members being surrounded by the plurality of first metal members or surrounding at least one of the plurality of first metal members, and the one or more second metal members generating location information by serving as a reference when identifying a location of the at least one of the plurality of first metal members based on the incident signal generated from the scanning with the electron beam,
wherein the one or more second metal members, when viewed from a normal direction to the principal faces, have a surface area larger than the a surface area of the plurality of first metal members, and have a length in the normal direction shorter than a length of the target, and
the control unit controls the deflector to scan the electron beam over the target, detects the plurality of first metal members based on the location information of the one or more second metal members acquired from the incident signal, and controls the deflector to irradiate the first metal member with the electron beam and generate X-rays.

2. The X-ray generation device according to claim 1, wherein a plurality of said one or more second metal members are arranged at evenly spaced intervals.

3. The X-ray generation device according to claim 1, wherein the plurality of first metal members are arranged at evenly spaced intervals.

4. The X-ray generation device according to claim 1, comprising at least two said one or more second metal members,
wherein one of the one or more second metal members has location information indicative of a location of the other of the one or more second metal members.

5. The X-ray generation device according to claim 1, wherein the one or more second metal members have a configuration indicative of a direction in which the plurality of first metal members are arranged.

6. The X-ray generation device according to claim 1, wherein the one or more second metal members are arranged to cover the substrate and have a plurality of substantially circular or polygonal shaped apertures containing the plurality of first metal members.

7. The X-ray generation device according to claim 6, wherein each of the apertures is formed to include inside a first of the plurality of metal members.

8. The X-ray generation device according to claim 6, wherein each of the apertures has a depression formed in a concave shape from an open end of each of the apertures.

9. The X-ray generation device according to claim 6, wherein the control unit detects the open end of each of the apertures, determines a center of each of the apertures, and specifies the location of the plurality of the first metal members.

* * * * *